US007332158B2

(12) United States Patent
Yang

(10) Patent No.: US 7,332,158 B2
(45) Date of Patent: *Feb. 19, 2008

(54) COMPOSITIONS AND TREATMENTS FOR MYELOSUPPRESSION BY EX VIVO ACTIVATED IMMUNE CELLS

(76) Inventor: Demao Yang, 1921 Rock St., Suite 16, Mountain View, CA (US) 94043

( * ) Notice: Subject to any disclaimer, the term of this patent is extended or adjusted under 35 U.S.C. 154(b) by 498 days.

This patent is subject to a terminal disclaimer.

(21) Appl. No.: 10/939,168

(22) Filed: Sep. 10, 2004

(65) Prior Publication Data

US 2005/0112105 A1 May 26, 2005

Related U.S. Application Data

(63) Continuation-in-part of application No. 10/159,148, filed on May 29, 2002, now Pat. No. 7,048,922.

(51) Int. Cl.
*A61K 35/14* (2006.01)
*C07K 14/475* (2006.01)
*C07K 14/55* (2006.01)

(52) U.S. Cl. .............. 424/93.7; 514/12; 530/351; 530/399

(58) Field of Classification Search ............ None
See application file for complete search history.

(56) References Cited

U.S. PATENT DOCUMENTS

| | | |
|---|---|---|
| 5,015,664 A | 5/1991 | Green |
| 5,047,421 A | 9/1991 | Green |
| 5,108,760 A | 4/1992 | Irr et al. |
| 5,506,267 A | 4/1996 | Aono et al. |
| 5,525,232 A | 6/1996 | Veiro et al. |
| 5,550,161 A | 8/1996 | Green |
| 5,616,612 A | 4/1997 | Ayral-Kaloustian et al. |
| 5,631,219 A * | 5/1997 | Rosenthal et al. ........... 514/6 |
| 5,643,786 A | 7/1997 | Cohen et al. |
| 5,658,945 A | 8/1997 | Ayral-Kaloustian et al. |
| 5,766,920 A | 6/1998 | Babbitt et al. |
| 5,932,446 A | 8/1999 | Gallagher et al. |
| 5,968,513 A | 10/1999 | Gallo et al. |
| 5,994,126 A | 11/1999 | Steinman et al. |
| 6,008,042 A | 12/1999 | Dixit et al. |
| 6,010,878 A | 1/2000 | Dixit et al. |
| 6,010,905 A | 1/2000 | Cohen et al. |

(Continued)

FOREIGN PATENT DOCUMENTS

EP 1077254 2/2001

(Continued)

OTHER PUBLICATIONS

Dallaporta et al. Plasma membrane potential in thymocyte apoptosis. J Immunol 162: 6534-6542, 1999.*

(Continued)

*Primary Examiner*—Bridget E. Bunner
(74) *Attorney, Agent, or Firm*—Bardi & Associates, PLLC

(57) ABSTRACT

The disclosure includes protocols of activating and administering human blood cells to myelosuppressed patients, including patients treated for cancer, e.g., by chemotherapy or radiation. The protocol may include culturing blood cells in the presence of a cytokine and an ionophore.

34 Claims, 6 Drawing Sheets

U.S. PATENT DOCUMENTS

| | | | |
|---|---|---|---|
| 6,033,661 | A | 3/2000 | Smith et al. |
| 6,074,639 | A * | 6/2000 | Bauer et al. ............. 424/93.71 |
| 6,187,821 | B1 | 2/2001 | Fujita et al. |
| 6,203,787 | B1 | 3/2001 | Thompson et al. |
| 6,294,169 | B1 | 9/2001 | Dixit et al. |
| 6,340,461 | B1 | 1/2002 | Terman |
| 6,352,694 | B1 | 3/2002 | June et al. |
| 7,048,922 | B2 | 5/2006 | Yang |
| 7,172,869 | B2 | 2/2007 | June et al. |
| 2001/0027215 | A1 | 10/2001 | Perrine |
| 2004/0101519 | A1 | 5/2004 | June et al. |
| 2005/0112105 | A1 | 5/2005 | Yang |

FOREIGN PATENT DOCUMENTS

| | | |
|---|---|---|
| WO | WO 95/20649 | 8/1995 |
| WO | WO 96/23060 | 8/1996 |
| WO | WO 98/06823 | 2/1998 |
| WO | WO 01/34788 | 5/2001 |
| WO | WO 01/62092 | 8/2001 |
| WO | WO 02/36748 | 5/2002 |

OTHER PUBLICATIONS

Furlong et al. Induction of apoptosis by valinomycin: mitochondrial permeability transition causes intracellular acidification. Cell Death Different 5: 214-221, 1998.*

Gwag et al. Calcium ionophores can induce either apoptosis or necrosis in cultured cortical neurons.Neuroscience. 90(4):1339-1348, 1999.*

Sigma Chemical Company Catalog. "Ionophores", pp. 587-589, 1995.*

Calbiochem Catalog. 2000-2001. "Ionophores", pp. 1, 91, 208, 262, 310, 369, 403, 412, 483, 486, 520, 554, 912.*

Ehrdahl et al. Ca2+ transport properties of ionophores A23187, ionomycin, and 4-BA23187 in a well defined model system. Biophysical J 66: 1678-1693, 1994.*

Abramov et al. Actions of ionomycin, 4-BrA23187 and a novel electrogenic Ca2+ ionophore on mitochondria in intact cells. Cell Calcium 33: 101-112, 2003.*

Elgert, K. Immunology, understanding the immune system. New York: Wiley-Liss, Inc., 1996; p. 24-26.*

Armitage, "Emerging Applications of Recombinant Human Granulocyte-Macrophage Colony-Stimulating Factor", *Blood*, 92(12); 4491-4508, Dec. 15, 1998.

Bagby, "Production of Multi Lineage Growth Factors by Hematopoietic Stromal Cells: An Intercellular Regulatory Network Involving Mononuclear Phagocytes and Interleukin-1," *Blood Cells*, 13; 147-159, 1987.

Bedrosian et al., "Granulocyte-Macrophage Colony-Stimulating Factor, Interleukin-2, and Interleukin-12 Synergize With Calcium Ionophore to Enhance Dendritic Cell Function," *Journal of Immunotherophy*, 23(3); 311-320, May-Jun. 2000.

Brugger et al., "Ex Vivo Expansion of Enriched Peripheral Blood CD34+ Progenitor Cells by Stem Cell Factor, Interleukin-1beta, IL-6, IL-3, Interferon-gamma, and Erythropoietin", *Blood*, 81; 2579-2584, 1993.

Champlin et al., "Treatment of Refactory Aplastic Anemia With Recombinant Human Granulocyte-Macrophage-Colony-Stimulating Factor," *Blood*, 73(3); 694-699, Feb. 15, 1989.

Chen et al., "Ex Vivo Immunotherapy for Patients with Benzene-induced aplastic Anemia", *J. Hematotherapy and Stem Cell Research*, 12(5); 505-514, 2003.

Chopra et al., "Interleukin 2, Interleukin 2 Receptor, and Interferon-yamma Synthesis and mNRA Expression in Phorbol Myristate Acetate and Calcium Ionophore A23187-Simulated T Cell From Elderly Humans," *Clinical Immunology and Immunopathology*, 53; 297-308, Nov. 1989.

Cooley et al., "Cytokine Activity after human bone marrow transplantation," *British Journal of Haematology*, 73(3); 341-347, 1989.

Czerniecki et al., "Calcium Ionophore-Treated Peripheral Blood Monocytes and Dendritic Cells Rapidly Display Characteristics of Activated Dentritic Cells," *Journal of Immunology*, 59(8); 3823-3837, Oct. 15, 1997.

Du et al., "Intrleukin-11: Review of molecular, Cell Biology, and Clinical Use", *Blood*, 89; 3897-3908, 1997.

Ettinghausen et al., "Hematologic Effects of Immunotherapy With Lymphokine-Activated Killer Cells and Recombinant Interleukin-2 in Cancer Patients," *Blood*, 69(6); 1654-1660, Jun. 1987.

Faries et al., "Calcium Signaling inhibits interleukin-12 production and activates CD83+ dendritic cells that induce Th2 cell development," *Blood*, 98(8); 2489-2497, Oct. 15, 2001.

Ferrara et al., "Graft-Versus-Host Disease," *The New England Journal of Medicine, Mechanisms of Disease*, 324 (10);667-674, Mar. 7, 1991.

Fibbe et al., "Biology of IL-8-Induced Stem Cell Mobilization", *Annuals New York Academy of Sciences*, 96(19) : 71-82, 1999.

Fibbe et al., "Human Fibroblasts Produce Granulocyte-CSF, Macrophage-CSF, and Granulocyte-Macrophage-CSF Following Stimulation by Interleukin-1 and Poly(R1).Poly(rC)," *Blood*, 72(3); 860-866, Sep. 1988.

Fujimori et al., "Effect of Lymphokine-Activated Killer Cell Fraction on the Development of Human Hematopoietic Progenitor Cells," *Cancer Res*, 48(3); 534-538, Feb. 1, 1988 (abstract only).

Ganser et al., "Effect of Recombinant Human Interleukin-3 in Patients With Normal Hematopoiesis and in Patients With Bone Marrow Failure," *Blood*, 6(4); 666-676, Aug. 15, 1990.

Guinan et al., A Phase I/II Trial of Recombinant Granulocyte-Macrophage Colony-Stimulating Factor for Children With Aplastic Anemia, *Blood*, 76(6); 1077-1082, Sep. 15, 1990.

Halpérin et al., "Severe Acquired Aplastic Anemia in Children: 11-Year Experience With Bone Marrow Transplantation and Immunosuppressive Therapy," *American Journal of Pediatric Hematololy/Oncology*, 11(3); 304-309, 1989.

Hestdal et al., "In Vivo Effect of Interleukin-1α on Hematopoiesis: role of colony-Stimulating Factor Receptor Modulation", *Blood*, 80(10); 2486-2494, 1992.

Hunt et al., "Lanthaide-Ion Transport Across Phospholipid Vesicular Membranes: A Comparison of Alamethicin 30 and A23187 Using 1H-NMR Spectroscopy," *Bioscience Reports 2*, pp. 921-928, 1982.

Hyono et al., "Fluorescence Energy Transfer Between Ionophore, A23187, and Membrane Proteins of Isolated Outer and Cytoplasmic Membranes of a Gram-Negative," *Biochimica et Biophysica Acta*, 813; 111-116, 1985.

Jones et al., "Growth Factors in Haemopoiesis," *Baillieres Clin Haematol*, vol. 2, No. 1, pp. 83-111, Jan. 1989 (abstract only).

Kalf et al., "p-Benzoquinone, a Reactive Metabolite of Benzene, Prevents the Processing of Pre-interleukins-1α and -1β to Active Cytokines by Inhibition of the Processing Enzymes, Calpain, and Interleukin-1β Converting Enzyme," *Environmental Health Perspectives*, 04, Supp. 6; 1251-1256, Dec. 1996.

Kojima et al., "Treatment of Aplastic Anemia in Children With Recombinant Human Granulocyte-Colony Stimulating Factor," *Blood*, 77(5), pp. 937-941, Mar. 1, 1991.

Kolber et al., "Fluorescence Study of the Divalent Cation-Transport Mechanism of Ionophore A23187 in Phospholipid Membranes," *Biophysical Society*, 36; 369-391, Nov. 1981.

Koski et al., "Calcium Ionophore-Treated Myeloid Cells Acquire Many Dendritic Cell Characteristics Independent of Prior Differentiation State, Transformation Status, or Sensitivity to Biologic Agents," *Blood*, 94(4); 1359-1371, Aug. 15, 1999.

Kuter et al., "Recombinant Human Thrombopoietin: basic biology and evaluation of clinical studies", *Blood*, 100(10); 3457-3469, Nov. 15, 2002.

Laughlin et al., "Hematopoietic Recovery Following High-Dose Combined Alkylating-Agent Chemotherapy and Autologous Bone Marrow Support in Patients in Phase-I Clinical Trials of Colony-Stimulating Factors: G-CSF, GM-CSF, IL-1, IL-2, M-CSF," *Ann Hematol*, 67(6); 267-276, Dec. 1993 (abstract only).

Liu et al., "Cellular Interactions in Hemopoiesis," *Blood Cells*, 13, pp. 101-110, 1987.

Li et al., "Thrombocytopenia caused by the development of antibodies to thrombopoietin", 98(12); 3241-3248, Dec. 1, 20001.

Niculescu et al., "Inhibition of the Conversion of Pre-interleukins-1α and 1β To Mature Cytokines by p-Benzoquinone, a Metabolite of Benzene," *Chemico-Biological Interactions*, 98; 211-222, 1995.

Nimer et al., "A Phase I/II Study of Interleukin-3 in Patients With Aplastic Anemia and Myelodysplasia," *Experimental Hematology*, 22; 875-880, 1994.

Nobrega et al., "Naturally Activated and Resting T Cells Differ in Their Activation Requirements For Growth and Secretory Activities," *Cellular Immunology*, 125(1); 120-129, Jan. 1990.

Passweg et al., "Bone Marrow Transplantation for Severe Aplastic Anemia: Has Outcome Improved?," *Blood*, 90(2); 858-864, Jul. 15, 1997.

Rodriguez et al., "Regulation of Apoptosis in Interleukin-3-Dependent Hemopoietic Cells by Interleukin-3 and Calcium," *The EMBO Journal*, 9; 2997-3002, 1990.

Rodriguez et al., "Interleukin-6 ddeficiency affects bone marrow stromal precursors, resulting in defective hematopoietic support", *Blood*, ;103(9): 3349-54, 2004.

Roros et al., "Calcium ionophore and cytokine treatment of human peripheral blood myeloid cells produces dendritic cells with an enhanced abaility to sensitize autologous CD8+ T cells to tumor antigens in a single culture stimulation," Proceedings of the Annual Meeting of the American Association for Cancer Research, New York, NY, 38;631, Apr. 12, 1997.

Rosenfeld et al., "Intensive Immunosuppression With Antithymocyte Globulin and Cyclosporine as Treatment for Severe Aplastic Anemia," *Blood*, 85(11); 3058-3065, Jun. 1, 1995.

Setti et al., "The Induction of Distinct Cytokine Cascades Correlates With Different Effects of Granulocyte-Colony Stimulating Factor and Granulocyte/Macrophage-Colony-Stimulating Factor on the Lymphocyte Compartment in the Course of High-Dose Chemotherapy for Breast Cancer," *Cancer Immunol Immunother*, 48(6); 287-296, Sep. 1999 (abstract only).

Socié et al., "Malignant Tumors Occurring After Treatment of Aplastic Anemia," *New England Journal of Medicine*, 329(16); 1152-1157, Oct. 14, 1993.

Sonoda et al., "Multilineage Response in Aplastic Anemia Patients Following Long-Term Administration of Filgrastim (Recombinant Human Granulocyte Colony Stimulating Factor)," *Stem Cells*, 11; 543-554, 1993.

Waclavicek et al., "Calcium Ionophore: A Single Reagent for the Differentiation of Primary Human Acute Myelogenous Leukemia Cells Towards Dendritic Cells", *Brit. J. Haematol.*, 114(2); 466-473, 2001.

Westers et al., "A23187/IL-4 Cultural Leukemic Dendritic Cells Stimulate Autologous T Cell-Mediated Apoptosis of Acute Myeloid Leukemic Blasts," *Blood*, 98(11) Part 1, pp. 121a, Nov. 16, 2001.

Yang, "Response", *Stem Cells and Development*, 13(2); 162-163, Apr. 2004.

Young et al., "The Pathophysiology of Acquired Aplastic Anemia," *New England Journal of Medicine, Mechanisms of Disease*, 336(19) 1365-1372, May 8, 1997.

Young et al., "The Treatment of Severe Acquired Aplastic Anemia," *Blood*, 85(12); 3367-3777, Jun. 15, 1995.

Lipscomb et al., "Dendritic Cells: Immune Regulators in Health and Disease," Physiol. Rev., 82, Jan. 2002.

Shah "Why do we Still Use Serum in the Production of Biopharmaceuticals?", Brown et al., (eds.): Animal Sera. Animal Sera Derivatives and Substitutes Used in the Manufacture of Pharmaceuticals: Viral Safety and Regulator Aspects. Dev. Bio. Stand. Basel, Karger, 1999, vol. 99, pp. 17-22.

\* cited by examiner

COMPOSITIONS AND TREATMENTS FOR MYELOSUPPRESSION BY EX VIVO ACTIVATED IMMUNE CELLS

CROSS-REFERENCE TO RELATED APPLICATIONS

This present patent application is a continuation-in-part of U.S. patent application Ser. No. 10/159,148, filed May 29, 2002, now U.S. Pat. No. 7,048,922 which is hereby incorporated by reference herein. This present patent application is also related to copending U.S. patent application Ser. No. 10/939,302, filed Sep. 10, 2004.

BACKGROUND OF THE INVENTION

1. Field of the Invention

This invention relates to therapies for myelosuppressed patients, including aplastic anemia, anemia and thrombocytopenia. In particular, this invention relates to ex vivo activated immune cells as therapies for myelosuppressed patients. Furthermore, the invention relates to approaches to activate cells and corresponding cell culture approaches.

2. Background

Aplastic anemia is a disease characterized by ineffective hematopoiesis in a myelosuppressed patient. Patients have varying degrees of abnormalities in production of all blood cell types. Although in most cases, the cause of the disease is unknown, radiation, benzene-based compounds, viruses (e.g., hepatitis), environmental toxins, and over the counter and prescription medications have been suspected to cause myelosuppression by causing damage bone marrow, thereby leading to apoptosis of marrow stem cells. Regardless of the underlying causes, patients show similar clinical manifestations and disease progression courses. Aplastic anemia affects primarily young men and older persons of both genders. Annually, two to six per million worldwide develop this disorder, with a higher prevalence of incidences in the Orient as compared to Europe or the United States. Several causal phenomena are hypothesized for aplastic anemia: congenital, pregnancy, viral, and drugs and chemicals.

The most frequently cited causal agent of aplastic anemia is drugs or chemical exposure, which leads to the myelosuppression that underlies aplastic anemia. Some agents, such as chloramphenicol, benzene, ionizing radiation, and antineoplastic agents, cause an aplasia that is dose-related in severity from person-to-person. In these cases, marrow recovery usually occurs after withdrawal of the causal agent. Other agents, including pesticides and some anticonvulsants and antimicrobials, cause a reaction which is not dose-related and, therefore, cannot be predicted with hematological monitoring during administration. During administration of drugs, aplasias may occur even after cessation of drug therapy. In contrast to patients with idiopathic aplastic anemia, those with drug or toxin exposure exhibit similar clinical and demographic characteristics, have a similar prognosis, and a more-or-less uniform response to therapy.

In the case of benzene-induced aplastic anemia, mild to moderate disease symptoms usually disappear after patients cease being exposed to benzene. However, for patients with severe bone marrow failure or who continually need blood transfusions, effective and safe treatment has not often been heretofore available. To date, bone marrow transplantation is the only known cure.

Mild aplastic patients are often treated with as little therapy as possible. The rationale for minimum treatment for mildly aplastic patients is to remove the causal agent, thereby enabling spontaneous recovery. In young patients with severe anemia, bone marrow transplantation with an HLA-matched donor is the treatment of choice. Bone marrow transplantation effects complete remission in nearly 80% of cases. However, survival decreases to 10-20% when the donor and recipient are mismatched at two or more loci. Complications associated with transplantation include graft rejection, acute or chronic graft-versus-host disease, infection, and other miscellaneous organ specific damage. Marrow transplant recipients also have an increased long-term risk for developing subsequent solid tumors.

Indeed, bone marrow contains many of the cells involved in blood production (called hematopoiesis) and in immune function. Hematopoiesis involves many different cell types from a variety of lineages. A restoration of multiple cell lineages is useful for the effective function of the blood system. Suppression or damage to these cells can thus affect blood and/or immune function. Myelosuppression is a condition in which bone marrow cell activity is decreased, and can result in fewer red blood cells, white blood cells, and/or platelets. A pronounced shortage of white blood cells is leucopenia, and a shortage of neutrophils, which are a type of white blood cells, is termed neutropenia. Myelosuppression is probably the most common side effect of chemotherapy in cancer patients, and may lead to leucopenia, neutropenia and/or thrombocytopenia. Or various medical conditions can lead to temporary or chronic myelosuppression, which can be induced, or may result from pathophysiological conditions.

Thrombocytopenia is a condition in which the number of platelets in the blood is abnormally low, and may lead to abnormal bleeding. Thrombocytopenia purpura is a type of thrombocytopenia. Anemia and bleeding may be associated with thrombocytopenia. Severe and chronic thrombocytopenia is a complication of cancer treatment, and can be difficult to treat.

Certain growth factors have conventionally been used in attempts to treat myelosuppression, and complications such as febrile neutropenia, anemia, and bleeding, that are caused by standard-dose chemotherapy respectively. For example, factors such as G-CSF, erythropoietin and interleukin-11 have been used (James O. Armitage. Emerging Applications of Recombinant Human Granulocyte Macrophage Colony-Stimulating Factor, Blood, 92: 4491-4508, 1998; David J. Kuter and C. Glenn Begley. Recombinant human thrombopoietin: basic biology and evaluation of clinical studies. Blood, 100: 3457-3469, 2002; Xunxiang Du and David A. Williams. Interleukin-11: Review of Molecular, Cell Biology, and Clinical Use. Blood 89: 3897-3908, 1997.). However, because administration of more dose-intensive chemotherapy regimens has been pursued for better therapeutic efficacy, greater degrees of acute and prolonged myelosuppression are increasingly being observed. Severe and prolonged myelosuppression often resists the treatment of the growth factors and is managed predominantly by blood transfusion and modification of the chemotherapy dose. Moreover, thrombocytopenia associated with severe and prolonged myelosuppression is particularly difficult to treat because IL-11 (the only drug approved by FDA for treatment of chemotherapy-induced thrombocytopenia) only has a modest effect on platelet production. Thrombopoietin has been identified as a promising growth factor capable of promoting survival and maturation of megakaryocyte progenitors and platelet release in cancer patients, however, early clinical trials indicate that thrombopoietin can be antigenic in some patients, resulting in exacerbation of the disease (David J. Kuter and C. Glenn Begley. Recombinant human thrombopoietin: basic biology and evaluation of clinical studies. Blood 100, 3457-3469, 2002; Junzhi Li, Chun Yang, Yuping Xia, Amy Bertino, John Glaspy, Michael Roberts, and David J. Kuter. Thrombocytopenia caused by the development of antibodies to thrombopoietin. Blood, 98, 3241-3248, 2001.). The value of this agent in preventing and reversing severe thrombocytopenia has not been established.

Thus, while chemotherapy and radiotherapy are widely used for treatment of cancer, and as a part of procedure for bone marrow and stem cell transplantation, the efficacy of these therapies is often closely correlated with side effects; the most common side effect is myelosuppression. Mild to modest myelosuppression induced by chemotherapy and radiotherapy usually recovers either spontaneously after discontinuation of the therapy or after therapy with growth factors. But severe myelosuppression rarely recovers and often results in infection, bleeding and even death. Unfortunately, the four FDA-approved growth factors (G-CSF, GM-CSF, Interleukin-11 and Erythropoietin) that are routinely used to accelerate recovery of blood production are often not effective for severe and/or chronic myelosuppression, and the recovery of multilineage hematopoiesis.

SUMMARY OF THE INVENTION

The present disclosure describes materials and methods using cultured (activated) blood cells for treating myelosuppressed patients, and patients with blood deficiencies, such as anemia, aplastic anemia and/or thrombocytopenia. Such approaches include treatments for severe and/or chronic myelosuppression, and the recovery of multilineage hematopoiesis.

One embodiment of the invention is a process of treating a myelosuppressed patient having blood deficiencies associated with the myelosuppression, involving administering ex vivo cultured blood cells to the patient to increase concentrations of blood components. Another embodiment is a process of treating a human patient having blood deficiencies associated with a cancer treatment, that involves administering a therapeutically effective amount of ex vivo cultured blood cells to the patient to increase concentrations of blood components.

In another embodiment, a quantity of blood cells effective to treat blood deficiencies when injected into a patient is provided. The quantity of blood cells may be cultured in the presence of a cytokine and an ionophore. The cytokine and ionophore may be present in effective concentrations. The cytokine may comprise interleukin-2 and macrophage-colony stimulating factor. The ionophore may comprise A23187.

In another embodiment, this disclosure provides a process of treating blood deficiencies in a patient, the treatment comprising administering ex vivo cultured blood cells to the patient. A therapeutically effective amount of blood cells may be administered to the patient. The blood cells may be autologous to the patient, allogeneic to the patient, or from an immunologically acceptable owner. The blood cells may further be cultured in the presence of a cytokine and an ionophore. The cytokine and ionophore may be present in effective amounts.

In yet another embodiment, this disclosure provides a method of culturing blood cells, the method comprising culturing the blood cells in the presence of a cytokine and an ionophore. The blood cells may be cultured in the presence, for example, of effective amounts of the cytokine and ionophore; may be cultured in a medium which may or may not comprise mammalian serum; may be cultured for a period, for example, between about 2 and 200 hours or longer; and may be cultured at a temperature, for example, between about 30 and 42 degrees C. The cytokine may include interleukin-2 and/or granulocyte macrophage-colony stimulating factor. The ionophore may include A23187.

DETAILED DESCRIPTION

Figure 1:
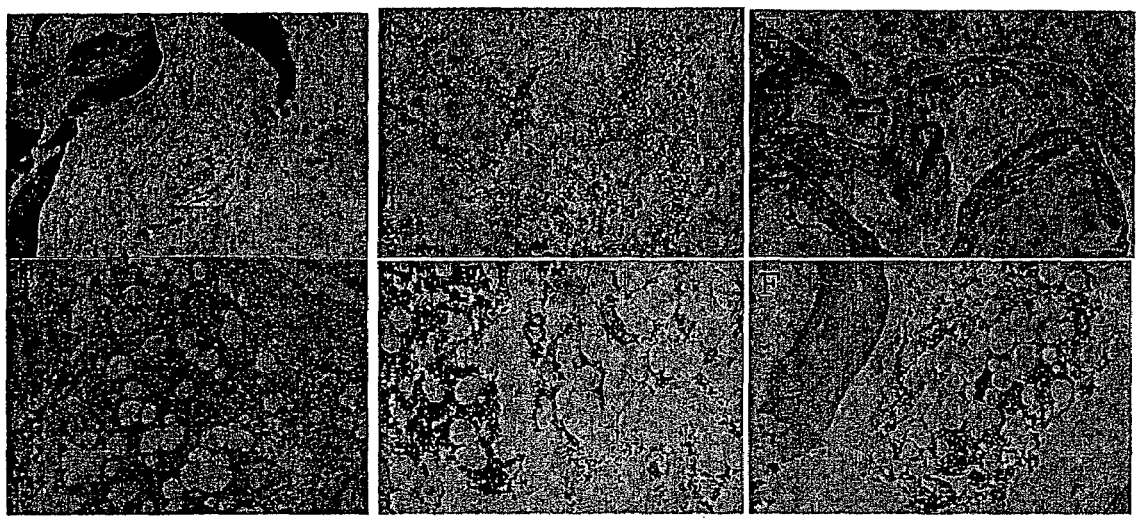
FIG. 1 shows low-power views of H&E stained bone marrow biopsies from three patients responsive to the present therapy. The views labeled as A, C and E are marrows from patients before treatment. In these views, early empty and impaired marrows implicate severe aplastic anemia. In the views denoted as B, D and F, the marrows are from the same patients after treatment. These marrows show much improved distribution and cellularity.

Described herein are materials and methods using cultured (activated) blood cells for treating myelosuppressed patients, and patients with blood deficiencies, such as anemia, aplastic anemia and/or thrombocytopenia. Such approaches include treatments for severe and/or chronic myelosuppression, and the recovery of multilineage hematopoiesis. Further, the inventor has disclosed certain uses of ex-vivo activated immune cells in the cross-referenced patent applications described as related, see above, and in Jiayu Chen, Weiwei Liu, Xiaohuai Wang, Huaiyu Chen, Jinming Wu, Yi Yang, Lubo Wu, Demao Yang, Ex Vivo Immunotherapy for Patients with Benzene-Induced Aplastic Anemia. Journal of Hematotherapy & Stem Cell Research. 12: 505-514, 2003; and in Demao Yang, Response, Stem Cells and Development. 13:162-163, 2004. The term cultured refers to a process of culturing cells, such as is customary in these arts. Culturing relates to creating conditions for cells that activate a cell's cellular machinery to produce a desired effect. Thus incubating a cell with certain factors to activate the cell is a culturing process, as is expanding cells ex vivo to increase their number. In contrast, a process of preserving or processing cells, e.g., by freezing or isolation of a particular type, is merely storage or sorting of the cells.

The term "therapeutically effective amount" is intended to include a sufficient quantity of the present activated blood cells to effect a statistically significant increase in blood cell counts when administered to a patient with blood deficiencies, i.e., a significantly low concentration of a natural blood component, such as red blood cells, white blood cells, platelets and other factors produced by the bone marrow and cells generated from the bone marrow. The cultured blood cells may be either from the patient or from an immunologically acceptable donor.

One protocol for activating blood cells via ex vivo culture includes obtaining a blood sample (e.g., 10-100 ml) from the patient, or an immunologically acceptable donor, separating blood cells from the blood sample, and culturing the separated blood cells. An "immunologically acceptable donor" is a person having tissues, to include blood cells, that do not have medically unacceptable levels of recipient reactions (e.g., hemolytic anemia, heart failure, renal failure). The blood cells may be separated from blood sera by protocols such as by centrifugation. The separated blood cells are then cultured under sterile conditions in a medium with one or more of a cytokine (to include cell stimulating factors) and an ionophore. Alternatively, other activating factors may be used, as described herein. The separated blood cells may be cultured in the media as specified above, for example, for periods between of greater than about 1 hour, in other embodiments between about 10 and 200 hours, between about 20 and 80 hours, or between about 30 and 60 hours and at a temperature, for example, between about 30 and 42 degrees C., in other embodiments between about 32 and 40 degrees C., or between about 37 and 38 degrees C. or any range subsumed therein. A person of ordinary skill in the art will recognize that other ranges of periods and temperatures within these explicit ranges are contemplated, and are within the present disclosure.

Certain embodiments are directed to the culturing of blood cells, and particularly peripheral blood mononuclear cell (PBMCs). The isolation of PBMCs has been practiced since the 1960's using various techniques after it was pioneered by Boyum, see Boyum, A. (1964) Nature, 204, 793-794, and Boyum, A. (1967) Scan, J. Lab. Clin. Invest Suppl. Some embodiments using PBMCs are advantageous because there is no need to isolate only one cell type. Thus complicated procedures for capturing essentially only one cell type may be avoided. Certain embodiments are directed to blood cultures of at least 2-20 cell types; ordinary artisans will recognize that all values within this explicit range are contemplated and described. It is recognized that procedures for isolating a single cell type may have some unintended impurities in the form of unwanted cell types, but such purified preparations essentially contain only one cell type. Further, it is recognized that in some instances a single cell type can be viewed as having a plurality of subtypes; nonetheless, such purified cultures capture a type of cell that has certain common features so that it may be characterized as a single cell type. Some of the processes described herein involve the capture a plurality of blood cell types having a number that may be subject to variation according to the particular equipment, operator, or method of numbering the cell types. Nonetheless, ordinary artisans, considering the processes and the various cell types in blood, can appreciate that certain embodiments of such processes will inevitably capture a number of cell types as described, e.g., at least 2-20.

Some embodiments relate to the culture of blood cells to produce a variety of blood cell types. Thus, regardless of the number of cell types or exact type of cells that are used to initiate blood cell culture, the processes of culturing may be directed so as to produce blood cells, and to produce a plurality of blood cell types. Blood cells are formed from certain pluripotent cells found in the bone marrow that are the progenitors of blood cells but do not become blood cells until they differentiate to exhibit functional characteristics identifiable as blood cells.

After being cultured, the activated blood cells may be washed (e.g., twice with sterile saline solution). Therapeutically effective amounts of the activated blood cells are then administered to patients. One acceptable method of administering the activated blood cells is intravenously. While the activated cells may be administered in a single dose, portions of the activated blood cells may also be administered over a period of time. For example, doses of the present activated blood cells may be administered to patients once per week for a period of four weeks. However doses of the present activated blood cells may be administered to patients at intervals of, for example, one-half week, ten days, 14 days, 21 days, other intermediate periods, or other effective periods. Moreover, the intervals may vary during the course of the treatment. For example, initially blood cell doses may be administered at daily, twice a week, weekly, and/or bi-weekly intervals. The dosages can be, for example, between about $1 \times 10^5$ to about $5 \times 10^8$ cells per treatment, which may depend on the patient's age and condition. The total time required for treatment (e.g., administering the present activated blood cells) may depend on the amount of activated blood cells available and patient response. Patient response can be measured, for example, in terms of return to normal blood cell counts and/or marrow histology as well as an overall improvement in health. Obviously, blood samples can be drawn from patients repeatedly during or after the initial treatment period so that additional activated blood cells can be obtained for further treatments. Furthermore, activated blood cells from an immunologically acceptable donor can be administered initially or administered for the entire duration of the treatment. Alternatively, blood cells from the patient, activated by the present protocol, may be administered after blood cells from an immunologically acceptable donor are initially administered.

Many ailments stemming from myelosuppression, e.g., blood deficiencies, can be treated by approaches described herein. In general, blood deficiencies involve a reduced concentration of blood components that originate from the bone marrow or from products, such as specific cell types, from the bone marrow. Blood deficiencies include, for example, anemia, aplastic anemia, and thrombocytopenia, e.g., thrombocytopenic purpura. Anemia can be considered broadly as a deficiency of a blood component or, in some contexts, as a deficiency of red blood cells. Aplastic anemia is a deficiency of peripheral blood elements. Thrombocytopenic purpura, such as idiopathic thrombocytopenic purpura, involves a deficiency in platelet number.

As a specific example, the discussion below, and also in Example 1, describes aplastic anemia in some detail, although the treatment methods can be applicable more broadly. For instance, thrombocytopenia purpura is also addressed herein, e.g., in Example 2, as is myelosuppression caused by cancer treatments, e.g., in Example 3. And the restoration of multilineage hematopoiesis following myelosuppression is described and discussed below, e.g., in Example 4.

The most current definition of severe aplastic anemia is marked pancytopenia with at least two of the following: 1) granulocytes less than 500/microliter, 2) platelets less than 20,000/microliter, 3) anemia with corrected reticulocyte count less than 1%, plus markedly hypoplastic marrow depleted of hematopoietic cells. Moderate aplastic anemia generally involves a hypocellular bone marrow and cytopenia in at least two cell lines not in the severe range. Onset is insidious and the initial complaint may be progressive fatigue and weakness due to the anemia, followed in some cases by hemorrhage. The hemorrhage is usually from the skin and mucosal linings, due to thrombocytopenia. Infection is rare despite the severe neutropenia. Physical examination reveals pallor and possibly bruising or petechiae. Aplastic anemia patients exhibit no lymphadenopathy or splenomegaly. Fever may or may not be present. Peripheral blood assays show pancytopenia. The presence of immature red and white blood cells strongly argues against aplastic anemia.

Red blood cells may be mildly macrocytic due to increased erythropoietic stress and they usually are normocytic and normochromic. The corrected reticulocyte count is very low or zero, indicating a lack of erythropoiesis. Bleeding time may be prolonged even with normal coagulation parameters. Patients have an increased serum iron and a normal transferrin, resulting in an elevated transferrin saturation. Plasma iron clearance is decreased due to a reduction in erythropoiesis. Bone marrow aspirate may be dry. But a biopsy can show severe hypocellular or aplastic marrow with fatty replacement. Because there have been cases in which the initial marrow biopsy exhibited hypercellularity, more than one biopsy may be necessary for accurate diagnosis. A severe depression can be noted in all hematopoietic progenitor cells, including myeloid, erythroid, pluripotent cell lines, and megakaryocytes. Diagnosis generally is based on finding the classic triad of anemia, neutropenia, and thrombocytopenia in both blood and bone marrow specimens. X-rays may be needed to rule out bone lesions or neoplastic infiltrates. Magnetic resonance imaging has been useful in clearly defining hypoplastic marrow. Since the diagnosis is one of exclusion, all other causes of pancytopenia and other lab findings are usually ruled out before aplastic anemia can be diagnosed.

The basic defect in aplastic anemia is myelosuppression such that there is failure of production of all cell lines. Possible mechanisms of the pathogenesis of aplastic anemia include 1) defective or absent hematopoietic stem cells, 2) abnormal bone marrow microenvironment, 3) abnormal regulatory cells, and 4) suppression of hematopoiesis by immunologic cells.

While the pathophysiology of the disease is not yet completely clear, (Young et al., The pathophysiology of acquired aplastic anemia, N. Engl. J. Med. 1997; 336(19): 1365-1372 and Young et al., The treatment of severe acquired aplastic anemia, Blood. 1995; 85(12): 3367-3377) there is evidence to support the theory that aplastic anemia is an immune-mediated disease. Bone marrow transplantation and immunosuppressive therapy using combined anti-lymphocyte globulin and cyclosporine have been used for treatment (Rosenfeld et al., Intensive immunosuppression with antithymocyte globulin and cyclosporine as treatment for severe aplastic anemia, Blood 1995; 85(11): 3058-3065 and Halperin et al., Severe acquired aplastic anemia in children: 11-year experience with bone marrow transplantation and immunosuppressive therapy, Am. J. Pediatr. Hematol. Oncol. 1989; 11(3): 304-309). However, the therapy of immune suppression often has undesirable and severe side effects. Moreover, hematopoietic growth factors such as granulocyte colony-stimulating factor (Kojima et al., Treatment of aplastic anemia in children with recombinant human granulocyte-colony stimulating factor, Blood 1991; 77(5): 937-941 and Sonoda et al., Multilineage response in aplastic anemia patients following long-term administration of filgrastim (recombinant human granulocyte colony stimulating factor), Stem Cells 1993; 11: 543-554), granulocyte macrophage colony-stimulating factor (Champlin et al., Treatment of refractory aplastic anemia with recombinant human granulocyte-macrophage-colony-stimulating factor, Blood 1989; 73(3): 694-699 and Guinan et al., A phase I/II trial of recombinant granulocyte-macrophage colony-stimulating factor for children with aplastic anemia, Blood 1990; 76(6): 1077-1082), and Interleukin-3 (Ganser et al., Effect of recombinant human interleukin-3 in patients with normal hematopoiesis and in patients with bone marrow failure, Blood 1990; 76(4): 666-676 and Nimer et al., A phase I/II study of interleukin-3 in patients with aplastic anemia and myelodysplasia, Exp. Hematol. 1994; 22: 875-880) have provided only limited and transient effects.

Many patients respond to immunosuppressive therapy and there are abnormal levels of various immune molecules in aplastic patients. For instance, Interleukin-1, produced by macrophages, natural killer cells, B lymphocytes, and endothelial cells, plays a central role in both immune responses and regulation of hematopoiesis by inducing the release of erythroid and multipotent colony-stimulating factors from marrow stromal cells, regulating early progenitor cells and stimulating stem cell recovery following induced myelosuppression. Immune dysregulation in aplastic anemia consists of decreased natural killer cell activity, increased numbers of activated T suppressor cells and abnormal production of Interleukin-2 and gamma-Interferon.

Natural killer cells are large granular lymphocytes which lyse tumor cells or virus-infected target cells upon direct contact. Natural killer cells also produce gamma-interferon, Interleukin-2, and induces colony-stimulating activity. These cells may inhibit myeloid and erythroid colony formation under certain conditions. For instance, when exogenous growth factors are absent from a culture, natural killer cells normally produce cytokines and support hematopoiesis. However, optimal conditions induce natural killer cells to inhibit hematopoiesis. Natural killer cell activity in aplastic anemia patients returns to normal after hematopoietic recovery.

Gamma-Interferon is produced by activated lymphocytes and suppresses hematopoiesis. Although aplastic patients show an overproduction of gamma-Interferon, levels of gamma-Interferon decrease in response to immunosuppression. Interferons are potent inhibitors of hematopoietic colony formation—both through direct action on progenitor cells and indirect effects via accessory immune system cells.

Tumor necrosis factor-alpha is another cytokine which is in excess in aplastic anemia. It functions to inhibit colony growth of the normal hematologic progenitors. High tumor necrosis factor-alpha values correlate with decreased platelet, hemoglobin, and leukocyte counts. Tumor necrosis factor-alpha and gamma-Interferon may act synergistically to suppressor hematopoiesis.

Aplastic anemia patients produce gamma-Interferon and tumor necrosis factor-alpha in excess, show an inverted helper:suppressor T cell ratio, and have predominantly T suppressor cells in the bone marrow. These cells may mediate suppression of hematopoiesis via cytokine production. The bone marrow also has a higher proportion of cytotoxic T cells than peripheral blood. The clinical relevance of immune dysfunction is suggested by a decrease in activated lymphocytes following successful immunosuppressive therapy.

Mechanisms for acquired aplastic anemia in general, and mechanisms for benzene-induced aplastic anemia in particular, are not well understood. Nonetheless, both types of aplastic anemia share considerable similarities with respect to pathophysiology and clinical manifestations. There are presently two hypotheses to explain the mechanism of aplastic anemia, direct damage and immune-mediated. Both hypotheses are supported by data from experimental and clinical studies. Direct damage to bone marrow cells is thought to be responsible for temporary and reversible bone marrow failure following cytotoxic chemotherapy and radiotherapy. Immune-mediated bone marrow failure is more difficult to cure. In the case of benzene-induced aplastic anemia, the disease seems to be associated with both mechanisms. Evidence of direct damage to bone marrow cells is supported by the studies indicating that benzene is involved in inhibiting a number of biochemical processes of bone marrow cells. Specifically, benzene has been shown to damage stromal macrophages in bone marrow, thereby leading to deficient interleukin-1 production (Niculescu et al., Inhibition of the conversion of pre-interleukins-1[alpha] and 1[beta] to mature cytokines by p-benzoquinone, a metabolite of benzene, Chemico-Biological Interactions; 1995; 98: 211-222 and Kalf et al., p-benzoquinone, a reactive metabolite of benzene, prevents the processing of pre-interleukins-1[alpha] and -1[beta] to active cytokines by inhibition of the processing enzymes, calpain, and interluekin-1[beta] converting enzyme, Environmental Health Perspectives; 1996; 104 (suppl. 6): 1251-1256). Interleukin-1 is considered important for growth and differentiation of stem cells (Bagby, G. C., Production of multi lineage growth factors by hematopoietic stromal cells: an intercellular regulatory network involving mononuclear phagocytes and interleukin-1, Blood Cells 1987; 13:147-159 and Fibbe et al., Human fibroblasts produce granulocyte-CSF, macrophage-CSF and granulocyte-macrophage-CSF following stimulation by interleukin-1 and poly(rl).poly(rC), Blood 1988; 72(3): 860-866). However, there has been no report of prolonged response to treatments of hematopoietic growth factors, including interleukin-1.

Severe and chronic thrombocytopenia is a complication of cancer treatment and can be difficult to treat. But, as shown herein, e.g., in Example 3, such conditions may be successfully treated with cellular activation therapies. In Example 3, there were 12 patients who had already failed conventional intensive chemotherapy and/or irradiation therapy. All of these patients had platelet counts less than 20,000/mL. Among these patients, 6 also had lower leukocyte counts—despite prior intensive conventional therapy with G-CSF. To treat these patients, peripheral blood mononuclear cells (PBMCs) from healthy donors were cultured in vitro with a combination of growth factors and a calcium-mobilizing agent for two days and the activated cells were infused intravenously three times a week. After 1 to 4 weeks of the treatment, 10 patients with thrombocytopenia responded to this therapy with their platelet counts increased to 40,000/mL while all patients with low leukocyte count obtained higher levels of leukocytes. The therapy was safe and well tolerated with minimal side effects. The cultured cells produced a wide range of cytokines. The data associated with these studies shows that the therapies disclosed herein are useful to ameliorate thrombocytopenia, even when severe and chronic.

And, for example, myelosuppression can result in damage to the body's hematopoietic capabilities. Set forth herein is a cell-based immunotherapy to treat such myelosuppression, which is demonstrated using in a mouse model, see Example 4. In Example 4, syngeneic spleen cells and xenogeneic human peripheral mononuclear cells were cultured ex vivo with a combination of cytokines and a calcium mobilizing-agent for 2 days and the activated immune cells were injected intravenously to mice after receiving high-dose chemotherapy and irradiation, the treated mice showed enhanced survival and hematopoietic recovery. The therapy was highly effective that a single injection was able to simulate multilineage hematopoietic recovery and promote survival. In studying the mechanism, it was found that the ex vivo cultured immune cells produced multiple cytokines and that adherent cells are more potent than non-adherent cells in promoting survival. It was also found that the therapy was less able to mobilize existing stem cells in normal mice in comparison with G-CSF.

Medium.

Suitable media used in ex vivo activation provide essential nutrients for blood cells. These media generally comprise, for example, inorganic salts, amino acids, vitamins, and other compounds all in forms which can be directly utilized by blood cells. By way of illustration and not limitation, one suitable medium is RPMI 1640. However, other media, such as serum-free media AIM-V, will support blood cells in culture may be suitable as well. The medium may be supplemented with a mammalian serum, e.g., fetal bovine serum at levels between about 0.1 and 50%, between about 1 and 40%, or between about 5% and 15%, of the medium, by weight. One suitable formulation of RPMI, designated as a modified RPMI 1640 and available under catalog number 30-2001 from American Type Culture Collection, has the following ingredients:

| Inorganic Salts | (g/liter) |
| --- | --- |
| $Ca(NO_3)_2 \cdot 4H_2O$ | 0.10000 |
| $MgSO_4$ (anhydrous) | 0.04884 |
| KCl | 0.40000 |
| $NaHCO_3$ | 1.50000 |
| NaCl | 6.00000 |
| $Na_2HPO_4$ (anhydrous) | 0.80000 |

| Amino Acids | (g/liter) |
| --- | --- |
| L-Arginine (free base) | 0.20000 |
| L-Asparagine · $H_2O$ | 0.05682 |
| L-Aspartic Acid | 0.02000 |
| L-Cystine · 2HCl | 0.06520 |
| L-Glutamic Acid | 0.02000 |
| L-Glutamine | 0.30000 |
| Glycine | 0.01000 |
| L-Histidine (free base) | 0.01500 |
| Hydroxy-L-Proline | 0.02000 |
| L-Isoleucine | 0.05000 |
| L-Leucine | 0.05000 |
| L-Lysine · HCl | 0.04000 |
| L-Methionine | 0.01500 |
| L-Phenylalanine | 0.01500 |
| L-Proline | 0.02000 |
| L-Serine | 0.03000 |
| L-Threonine | 0.02000 |
| L-Tryptophan | 0.00500 |
| L-Tyrosine · 2Na•$2H_2O$ | 0.02883 |

-continued

| Amino Acids | (g/liter) |
|---|---|
| L-Valine | 0.02000 |

| Vitamins | (g/liter) |
|---|---|
| D-Biotin | 0.00020 |
| Choline Chloride | 0.00300 |
| Folic Acid | 0.00100 |
| myo-Inositol | 0.03500 |
| Nicotinamide | 0.00100 |
| p-Amino Benzoic Acid | 0.00100 |
| D-Pantothenic Acid (hemicalcium) | 0.00025 |
| Pyridoxine · HCl | 0.00100 |
| Riboflavin | 0.00020 |
| Thiamine · HCl | 0.00100 |
| Vitamin B-12 | 0.000005 |

| Other | (g/liter) |
|---|---|
| D-Glucose | 4.50000 |
| Glutathione (reduced) | 0.00100 |
| HEPES | 2.38300 |
| Phenol Red, Sodium Salt | 0.00500 |
| Sodium Pyruvate | 0.11000 |

1. Cytokines. One or more cytokines may be used to activate blood cells when cultured in the presence thereof. Cytokines are small proteins (usually in the range of 5-20 kD) that are released by cells and have specific effects on cell-cell interaction, communication, and behavior of other cells. Usually included as cytokines, are interleukins, lymphokines and signaling molecules such as tumor necrosis factor (TNF) and interferons. While natural cytokines can be used, recombinant produced cytokines produced, for example, by established nucleic acid expression systems are also contemplated. As such, modified and mutated forms of natural cytokines that maintain function can also be used. Exemplary cytokines, which may be suitable for some embodiments of the present invention, include:

A. Interleukins. A variety of naturally occurring polypeptides that affect functions of specific cell types and are found in small quantities. They are secreted regulatory proteins produced by lymphocytes, monocytes and various other cells and are released by cells in response to antigenic and non-antigenic stimuli. The interleukins, of which there are 16 identified to date, modulate inflammation and immunity by regulating growth, mobility and differentiation of lymphoid and other cells. Interleukins may be present in concentrations between about 10 and 50,000 IU/ml, about 100-5,000 IU/ml, or about 100-1,000 IU/ml. Alternatively an effective concentration of interleukins may be present. An effective concentration of interleukins is any concentration at which blood cells are activated by the present protocol.

i. Interleukin-1 (IL-1). IL-1 is a soluble protein (17 kD: 152 amino acids) secreted by monocytes, macrophages or accessory cells involved in the activation of both T lymphocytes and B lymphocytes and potentiates their response to antigens or mitogens. Biological effects of IL-1 include the ability to replace macrophage requirements for T-cell activation, as well as affecting a wide range of other cell types. At least two IL-1 genes are known and alpha and beta forms of IL-1 are recognized. IL-1 is released early in an immune system response by monocytes and macrophages. It stimulates T-cell proliferation and protein synthesis. Another effect of IL-1 is to cause fever.

ii. Interleukin-2 (IL-2). IL-2 is a hormone-like substance released by stimulated T lymphocytes. IL-2 causes activation and differentiation of other T lymphocytes independently of antigen. IL-2 stimulates the growth of certain disease-fighting blood cells in the immune system and is secreted by Th1 CD4 cells to stimulate CD8 cytotoxic T lymphocytes. IL-2 also increases the proliferation and maturation of CD4 cells themselves.

iii. Interleukin-3 (IL-3). IL-3 is a product of mitogen activated T-cells. IL-3 is a colony stimulating factor for bone marrow stem cells and mast cells. IL-3 is considered one of the hematopoietic colony stimulating factors.

iv. Interleukin-4 (IL-4). IL-4 is a soluble cytokine factor produced by activated T lymphocytes that promotes antibody production by causing proliferation and differentiation of B-cells. IL-4 induces the expression of class II major histocompatibility complex and fc receptors on B-cells. IL-4 also acts on T lymphocytes, mast cell lines, and several other hematopoietic lineage cells including granulocyte, megakaryocyte, and erythroid precursors, as well as macrophages.

v. Interleukin-5 (IL-5). IL-5 is a factor promoting eosinophil differentiation and activation in hematopoiesis. It also triggers activated B-cells for a terminal differentiation into Ig-secreting cells.

vi. Interleukin-6 (IL-6). IL-6 stimulates the growth and differentiation of human B-cells and is also a growth factor for hybridomas and plasmacytomas. It is produced by many different cells including T-cells, monocytes, and fibroblasts. IL-6 is a single chain 25 kD cytokine originally described as a pre B-cell growth factor, now known to have effects on a number of other cells including T-cells which are also stimulated to proliferate.

vii. Interleukin-7 (IL-7). IL-7 is a hematopoietic growth factor that promotes growth of B-cell precursors and is also co-mitogenic with interleukin-2 for mature T-cell activation. IL-7 is produced by bone marrow stromal cells.

viii. Interleukin-8 (IL-8). IL-8 is a cytokine that activates neutrophils and attracts neutrophils and T lymphocytes. IL-8 is released by several cell types including monocytes, macrophages, T lymphocytes, fibroblasts, endothelial cells, and keratinocytes by an inflammatory stimulus. IL-8 is a member of the beta-thromboglobulin superfamily and structurally related to platelet factor 4.

ix. Interleukin-9 (IL-9). IL-9 is a cytokine produced by T-cells, particularly when mitogen stimulated. IL-9 stimulates the proliferation of erythroid precursor cells (BFUE) and is thought to be a regulator of hematopoiesis. IL-9 may act synergistically with erythropoietin. The IL-9 receptor belongs to the hemopoietic receptor super family. IL-9 has been shown to enhance the growth of human mast cells and megakaryoblastic leukaemic cells as well as murine helper T-cell clones. Il-9 is a glycoprotein that is derived from T-cells and maps to human chromosome 5.

x. Interleukin-10 (IL-10). IL-10 is a factor produced by Th2 helper T-cells, some B-cells and LPS activated monocytes. It is a coregulator of mast cell growth.

xi. Interleukin-11 (IL-11). IL-11 is a pleiotropic cytokine, originally isolated from primate bone marrow stromal cell line, that has the ability to modulate antigen-specific antibody responses, potentiate megakaryocytes, and regulate bone marrow adipogenesis. IL-11 stimulates T-cell dependent B-cell maturation, megakaryopoiesis, and various stages of myeloid differentiation.

xii. Interleukin-12 (IL-12). IL-12 is a 75 kD heterodimeric cytokine composed of disulfide-bonded 40 kD and 35 kD subunits that was originally identified by its ability to induce cytotoxic effector cells in synergy with less than optimal concentrations of interleukin-2. IL-12 is released by macrophages in response to infection and promotes the activation of cell-mediated immunity. Specifically, IL-12 triggers the maturation of Th1 CD4 cells, specific cytotoxic T lymphocyte responses, and an increase in the activity of NK cells. Consequently, IL-12 is the initiator of cell-mediated immunity. It enhances the lytic activity of NK cells, induces interferon production, stimulates the proliferation of activated T-cells and NK cells. Is secreted by human B lymphoblastoid cells (NC 37).

xiii. Interleukin-13 (IL-13). IL-13 is a T lymphocyte-derived cytokine that produces proliferation, immunoglobulin isotype switching, and immunoglobulin production by immature B-lymphocytes. IL-13 is produced by activated T-cells, inhibits IL-6 production by monocytes, and also inhibits the production of other pro-inflammatory cytokines such as TNF, IL-1, and IL-8. IL-13 stimulates B-cells. The gene for IL-13 is located on human chromosome 5q in a gene cluster that also has the IL-4 gene.

xiv. Interleukin-14 (IL-14). IL-14 is a cytokine that induces B-cell proliferation, inhibits immunoglobulin secretion, and selectively expands certain B-cell subpopulations.

xv. Interleukin-15 (IL-15). IL-15 is a cytokine that stimulates the proliferation of T lymphocytes and shares biological activities with IL-2. Il-15 also can induce B lymphocyte proliferation and differentiation.

xvi. Interleukin-16 (IL-16). IL-16 is a cytokine produced by activated T lymphocytes that stimulates the migration of CD4-positive lymphocytes and monocytes.

B. Lymphokines. A lymphokine is a substance produced by a leucocyte that acts upon another cell. Examples are interleukins, interferon alpha, lymphotoxin (tumor necrosis factor alpha), granulocyte monocyte colony stimulating factor (GM-CSF).

i. Interferons (IFN) are a family of glycoproteins human cells which normally have a role in fighting viral infections by preventing virus multiplication in cells. Interferons may be present in the same concentrations as interluekins. Alternatively, effective concentrations of interferons may be present. Effective concentrations of interferons are contemplated to include any concentration at which blood cells are activated by the present protocol. IFN alpha is secreted by leucocytes and IFN gamma is secreted by fibroblasts after viral infection.

1. Interferon gamma is an interferon elaborated by T lymphocytes in response to either specific antigen or mitogenic stimulation.

2. Interferon alpha includes a number of different subtypes that are elaborated by leukocytes in response to viral infection or stimulation with double-stranded RNA. IFN-alpha-2A and—2B are protein products made by recombinant DNA techniques and are used as antineoplastic agents. Interferon-alpha is one of the type I interferons (interferon type I) produced by peripheral blood leukocytes or lymphoblastoid cells when exposed to live or inactivated virus, double-stranded RNA, or bacterial products. It is the major interferon produced by virus-induced leukocyte cultures and, in addition to its pronounced antiviral activity, causes activation of natural killer cells.

3. Interferon alfa-2a is a type I interferon consisting of 165 amino acid residues with lysine in position 23. This protein is produced by recombinant DNA technology and resembles interferon secreted by leukocytes. It is used extensively as an antiviral or antineoplastic agent.

4. Interferon alfa-2b is type I interferon consisting of 165 amino acid residues with arginine in position 23. This protein is produced by recombinant DNA technology and resembles interferon secreted by leukocytes. It is used extensively as an antiviral or antineoplastic agent.

5. Interferon beta is an interferon elaborated by fibroblasts in response to the same stimuli as interferon alpha. Interferon-beta is one of the type I interferons produced by fibroblasts in response to stimulation by live or inactivated virus or by double-stranded RNA. It is a cytokine with antiviral, antiproliferative, and immunomodulating activity.

6. Interferon-b2 (interleukin-6) is a cytokine that stimulates the growth and differentiation of human B-cells and is also a growth factor for hybridomas and plasmacytomas. It is produced by many different cells including T-cells, monocytes, and fibroblasts. INF-b2 is a single chain 25 kD cytokine originally described as a pre B-cell growth factor, now known to have effects on a number of other cells including T-cells, which are also stimulated to proliferate. INF-b2 is an inducer of acute phase proteins and a colony stimulating factor acting on mouse bone marrow.

7. Interferon gamma is elaborated by T lymphocytes in response to either specific antigen or mitogenic stimulation.

ii. Tumor necrosis factor (TNF) is a tumor-inhibiting factor present in the blood of animals exposed to bacterial lipopolysaccharide. TNF preferentially kills tumor cells in vivo and in vitro, causes necrosis of certain transplanted tumors in mice, and inhibits experimental metastases. Human TNF alpha is a protein of 157 amino acids and has a wide range of pro-inflammatory actions. TNF may be present in the same concentrations as interleukins. Alternatively, TNF may be present in an effective concentration.

An effective concentration of TNF is an concentration at which blood cells are activated by the present protocol.

C. Cell Stimulating Factors. Activating blood cells in the presence of one or more cell stimulation factors may be efficacious in alleviating aplastic anemia in the context of the present invention. Cell stimulating factors are contemplated to include such substances as granulocyte colony-stimulating factor granulocyte macrophage-colony stimulating factor and macrophage-colony stimulating factor. Cell stimulating factors may be present in concentrations between about 10 and 50,000 IU/ml, between about 10 and 10,000 IU/ml, or between about 10 and 1000 IU/ml. Alternatively, an effective concentration of cell stimulating factors may be present. An effective concentration of cell stimulating factors is any concentration at which blood cells are activated by the present protocol.
1. Granulocyte colony-stimulating factor (G-CSF): G-CSF are glycoproteins synthesized by a variety of cells and are involved in growth and differentiation of hematopoietic stem cells. In addition, these factors stimulate the end-cell functional activity of stem cells.
2. Granulocyte-macrophage colony-stimulating factor (GM-CSF): GM-CSF is an acidic. glycoprotein of 23 kD with internal disulfide bonds. GM-CSF is produced in response to a number of inflammatory mediators by mesenchymal cells present in the hemopoietic environment and at peripheral sites of inflammation. GM-CSF stimulates the production of neutrophilic granulocytes, macrophages, and mixed granulocyte-macrophage colonies from bone marrow cells and can stimulate the formation of eosinophil colonies from fetal liver progenitor cells.
3. Macrophage-colony stimulating factor (M-CSF): M-CSF is a cytokine synthesised by mesenchymal cells that stimulates pluripotent stem cells of bone marrow into differentiating towards the production of monocytes (mononuclear phagocytes). The compound stimulates the survival, proliferation, and differentiation of hematopoietic cells of the monocyte-macrophage series. It is a disulfide-bonded glycoprotein dimer with a mw of 70 kD and binds to a single class of high affinity receptor which is identical to the product of the c-fins proto-oncogene.

2. Ionophores. Ionophores are calcium or other cation specific reagents (such as polypeptrates) which can traverse a lipid bilayer and a lipid soluble. There are two classes of ionophores: carriers and channel formers. Carriers, like valinomycin, form cage-like structures around specific ions, diffusing freely through the hydrophobic regions of the bilayer. Channel formers, like gramicidin, form continuous aqueous pores through the bilayer, allowing ions to defuse therethrough. In addition to the foregoing, suitable ionophores for the present protocol may include A23187 (calcimycin), ionomycin, geldanamycin, monensin (Na-salt), nystatin, polymyxin-B sulfate, and rapamycin. It is believed that carriers, such as A23187, accumulate calcium cations in response to pH gradients. A23187 possesses a dissociating carboxylic acid group and catalyzes an electrically neutral exchange of protons for other cations across the membrane (Hyono et al., BBA 389, 34-46 (1985): Kolber and Haynes, Biophysics Journal, 36, 369-391 (1981); Hunt and Jones, Biosci. Rep., 2, 921-928 (1982)). Two molecules of A23187 are present as carboxylate anions, and are thus available to carry to protons, or equivalents, back across the membrane after releasing the transported divalent cation. If present, ionophores may be present in concentrations between about 1 and 10,000 ng/ml, between about 1 and 1000 ng/ml, or between about 10 and 500 ng/ml. Alternately, ionophores may be present in an effective concentration. An effective concentration of ionophores is any concentration at which blood cells are activated, but not overactivated, by the present protocol. Excessive concentrations of activating agents may not be effective in the treatment approaches described herein.

Use, Packaging and Distribution

The delivery of activated cells can provide a statistically significant improvement in clinical parameters of a patient. For example, the administration of cell activated as described herein can result in a statistically significant increase in white blood cell counts, red blood cell counts hemoglobin levels and platelet counts. In general, continuation of the treatment procedure as described herein can result in a return to normal blood levels. In some embodiments, after four treatments, the patient can have an increase in each of white blood cell counts, red blood cell counts and hemoglobin of at least about 20%, in other embodiments at least about 35% and in other embodiments at least about 50%. Similarly, in some embodiments, platelet counts can increase by at least about 25%, in other embodiments at least about 50%, and in further embodiments at least about 100%. A person of ordinary skill in the art will recognize that additional ranges of blood parameter improvement within the explicit ranges presented are contemplated and are within the present disclosure.

The activation compounds, such as one or more cytokines and/or one or more ionophore, can be mixed with an appropriate cell culture medium or a portion thereof for distribution. In alternative embodiments, one or more activation compounds can be packaged along with a cell culture medium or portions thereof for shipping. Similarly, a desired combination of activation compounds, such as one or more cytokines and one or more ionopores, can be packaged together for shipping, either mixed or in separate compartments. In any of these embodiments, the medium and/or activation compounds can be combined with any remaining medium components and/or activation compounds to form the desired medium for culturing cells under conditions to activate the cells. Also, in any of these embodiments, the compositions that are packaged together can include, for example, instructions for completing the cell culture medium with activation properties and/or instructions for performing the cell culturing.

The cell culturing can be performed at the facility that is treating the patient or the cell culturing to activate the cells can be performed at a remote location. In either case, the activated cells can be administered after a short period of time after harvesting from the cell culture to ensure that the cells remain viable. Alternatively, the cells can be stored under conditions that maintain the cells in a viable condition. For example, the cells can be stored at liquid nitrogen temperatures with a cryoprotectant. The cells can be prepared, for example using known procedures, at appropriate times for administration to the patient. For example, the cells can be suspended in a buffered saline solution for administration to the patient. Other known carriers, for example, can be used for delivery of the cells.

EXAMPLES

Example 1

Treatment of Aplastic Anemia

I. Patients

Eight patients with verified histories of from one to six years of occupational exposure to benzene were subjected to the present regimen after their consents were obtained. The makeup of the patients was one male and seven females and the ages of the patients ranged from 24 to 41. All patients experienced symptoms of weakness, dizziness, fainting, and accelerated heart rates. Among these patients, four were hospitalized due to acute symptoms with bleeding. The hospitalized patients required blood or platelet transfusions. The other four patients experienced chronic symptoms and were treated with standard therapies for four, six and 15 months, respectively. Bone marrow biopsies and aspiration samples were obtained from all patients to confirm hematopoiesis. Toxic levels of benzene were present in the blood and bone marrow of all patients.

II. Purification of Peripheral Blood Mononuclear Cells and Cell Culture

Peripheral blood mononuclear cells (PBMCs) were separated from patient blood samples (40-50 ml) by Ficoll-Hypaque centrifugation. The separated PBMCs were then placed in an appropriate volume (based on cell concentration) of RPMI 1640 with 10% fetal bovine serum under sterile conditions and cultured at $2\times10^6$ cells/ml for 48 hours in the presence of interleukin-2 (IL-2) at 500 IU/ml (Chiron, Emeryville, Calif.), granulocyte macrophage-colony-stimulating factor (GM-CSF) at 200 IU/ml (Immunex, Seattle, Wash.), and calcium ionophore A23187 at 100 ng/ml (Sigma, St. Louis, Mo.). At the end of the culture period, adherent cells were scraped off the plastic surfaces of the culture vessels and harvested together with non-adherent cells. To harvest the cells, the cells were spun down to form a cell pellet. Different numbers of cells were obtained for different patients. The harvested cells were washed twice in saline solution and administered to the patients. After washing, the cells were resuspended in 5 to 10 mls of saline, with the volume determined by the number of cells. These suspensions were further diluted with 50 ml of saline before administering the cells to the patients.

Treatment Protocol

Activated allogeneic PBMCs were used for a single patient (HC) in the first three treatments because the patient had experienced low blood counts, severe bleeding and infection. For the other patients, activated PBMCs were intravenously administered with 50 ml saline to the patients. The treatment was repeated every week for at least four weeks. The number of cells administered to a particular patient depended on the number of cells obtained from the patient.

III. Results

Hematological Parameters

Hematological parameters, white blood cell counts, red blood cell counts, hemoglobin levels, and platelet counts, were monitored before and after the treatment for each patient and are shown in Table 1. Data from these patients indicated that the therapy was effective in enhancing the peripheral blood cell counts. Six patients experienced improvement of more than one subset listed and two patients had better platelet counts. The blood cell counts began to improve in most patients after two treatments and continued to improve throughout the time the present activated cells were administered. Seven of the eight patients improved to the extent that some of their hemological parameters reach normal levels or levels approaching normal after completion of four treatments. Although blood cell counts of the patients improved from the therapy in general, improvements were not uniformly achieved. Some patients experienced limited improvement in red blood cell counts, but dramatic improvement in platelet counts. It was noted that all patients' platelet counts were significantly increased.

Patient HC experienced more severe acute symptoms than the other patients. Additionally, patient HC had a bleeding problem as well. Because of the low yields of peripheral blood cells from patient HC, allogeneic PBMCs were used to stimulate patient HC's hematopoiesis. After three treatments using allogeneic cells, patient HC's blood counts began to improve. After the three treatments of allogeneic cells, autologous PBMCs were then used to continue the therapy. Although patient HC's hematological parameters were not corrected to normal levels after six treatments, patient HC continued to improve.

Discomfort due administering the present immunotherapy was mild to moderate. Five patients experienced no appreciable discomfort. Three patients experienced chilling, fevers between 37 and 39 degrees C., headaches, nausea, vomiting, and loss of appetite after cell infusion. However, these symptoms were transient, typically lasting one to two days. Aspirin was administered when patients experienced discomfort.

Bone Marrow Hematopoiesis

Bone marrow biopsies and aspiration samples were obtained from all patients before the therapy began and two weeks after the final treatment. As shown in FIG. 1, the histology of the bone marrow samples from three patients with the most severe samples indicated severe damage before the therapy was begun. After the therapy was administered, remarkable improvements in bone marrow histology were found. With respect to patient HC, however, the improvement observed in patient HC's bone marrow was not coupled with improved peripheral blood counts.

Blood Transfusion

Before beginning treatment, four of the eight patients experienced severe symptoms, coupled with bleeding. These four patients required periodic transfusions of whole blood or platelets before and during the therapy. After four treatments, however, none of the patients experienced bleeding and whole blood and platelet transfusions were not continued.

Duration

Figure 2:
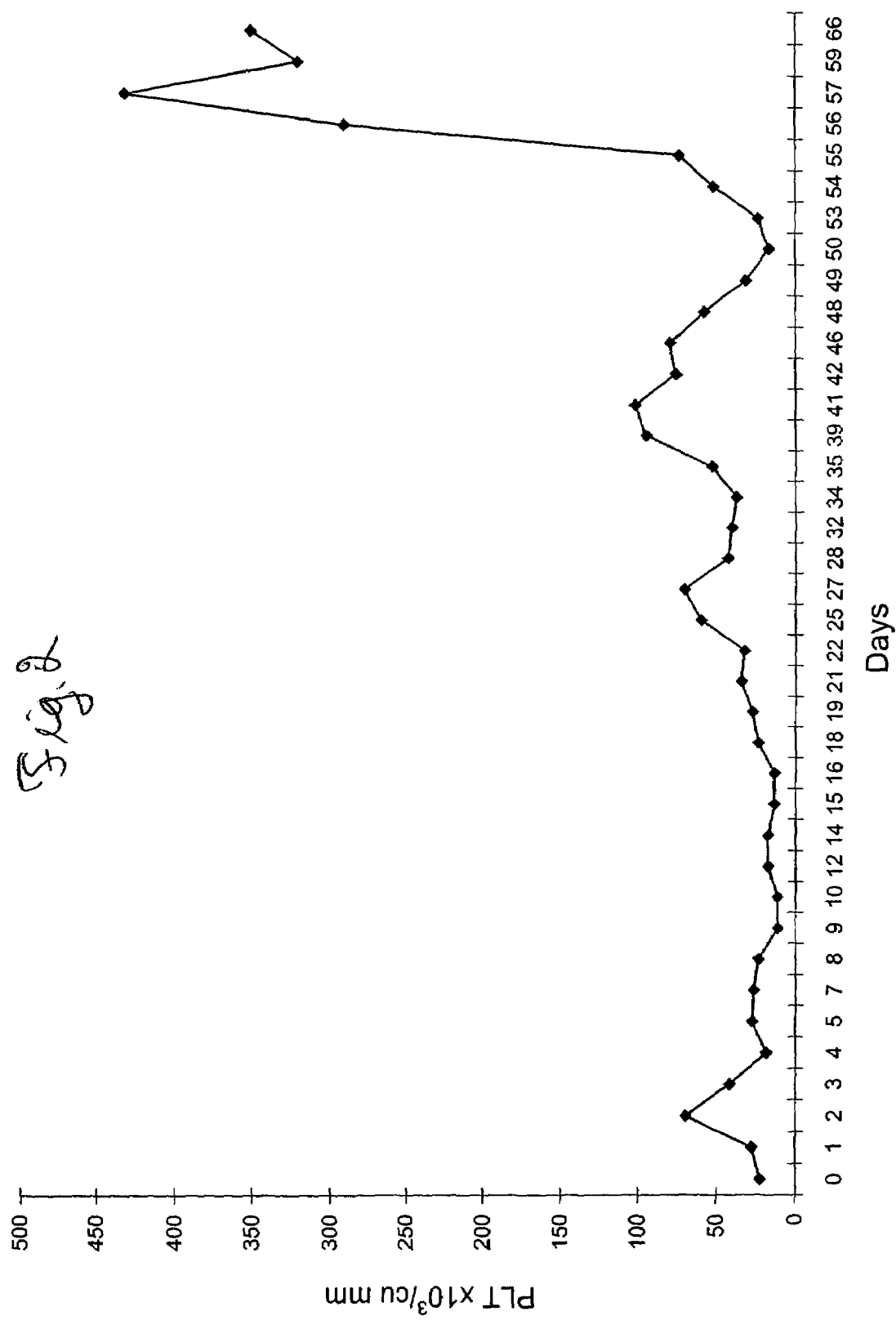
FIG. 2 is a plot of platelet count in platelets per cubic millimeter as a function of days after starting treatment with activated cells for a child patient with platelet deficiency.

The beneficial effects of the present cell-based therapy do not appear to be transient. All patients continued to have improved or stable hematological parameters after the therapy was discontinued. Some female patients experienced unstable blood counts during menstrual periods, but no patients experienced a relapse. Patient LC, who responded to the therapy, has experienced stable symptoms for more than two months since the final treatment (FIG. 2).

Discussion

The results of this study indicate that administering activated PBMCs to patients with aplastic anemia is highly effective. Some patients had close to normal bone marrow histologically, but had peripheral hematological parameters which were not as close to normal. To this end, it seemed that a time gap occurred between histological recovery of bone marrow and recovery of peripheral blood cell counts. Patients experiencing this gap were closely monitored and the patients' hematological parameters showed continued improvement. These patients sometimes took a few weeks or months to attain normal peripheral blood cell counts.

In analyzing the data generated by the study, it was noted that, among different compartments of the blood, increase in platelets was most evident, significant and rapid in patients benefiting from therapy. The initial increase in platelet counts was possibly due to the fact that platelets have a faster generation and differentiation interval. Other cell types of blood such as neutrophils, granulocytes and reticulocytes were also improved in agreement with the four parameters listed (data not shown). Platelet counts are likely more susceptible to benzene toxicity than other blood cells, but are the most responsive to the present therapy due to their faster generation interval.

Acquired aplastic anemia is a difficult disease to cure. However, the present immunosuppression therapy was very effective in treating this disease, for which bone marrow transplants are the only known cure heretofore. However, in spite of the success of bone marrow transplants, this therapy has serious complications, e.g., tumors, (Socie et al., Malignant tumors occurring after treatment of aplastic anemia, N. Eng. J. Med. 1993; 329(16): 1152-1157) and graft-versus-host disease (Ferrara et al., Graft-versus-host disease, N. Engl. J. Med. 1991(324); 324: 667-674). Moreover, many patients cannot obtain bone marrow transplants due to the expense of the procedure and/or the lack of compatible donors. To this end, a simple and effective therapy with fewer side effects is needed to treat aplastic anemia. The results of this study indicate that aplastic anemia can be effectively treated with minimal side effects. The present cell-based immunotherapy is believed to be applicable to other types of anemia and bone marrow disorders as well. These disorders include those experienced by HIV (human immunodeficiency virus)-infected patients after cocktail chemotherapy and cancer patients with bone marrow failure after chemotherapy and radiotherapy, inherited aplastic anemia, and idiopathic thrombocytopenic purpura.

While not wishing to be bound by a specific theoretical basis for the operation of this invention, it is presently believed that several phenomena may be responsible for the favorable responses of patients to the present immunotherapy. A first theory is that the activated cells secrete multiple (perhaps partially unknown) effective factors simultaneously. These multiple factors, when working in concert, may have a synergistic combined effect. A second factor hypothesized for the effectiveness of the present therapy is that some presently unknown key factors for hematopoiesis are produced by activated immune cells. These unknown factors may be responsible, at least in part, for the effectiveness of the present therapy. A third factor which might be involved is that immune cells are capable of traveling to bone marrow and of delivering cytokines to hematopoietic stem cells and to other precursor cells at close range. Moreover, the present activated immune cells may be able to remain in close proximity to the marrow for periods sufficient to effect microenvironment improvement in the bone marrow. A fourth factor which might be responsible for the effectiveness of the present therapy is that cell contact between immune cells and hematopoietic cells may be essential for hematopoietic cell growth and differentiation. A fifth factor might be that activated immune cells, even in small amounts, may contribute to prevent the immune system from adversely influencing hematopoiesis. Quantities of PCMBs from 10-100 ml of blood are relatively small. However, these small quantities exerted large effects on bone marrow histology and hematopoiesis.

The results of administering blood cells activated by the present protocol are unexpected in view of results from previous studies. With the exception of one study, Young et al. (note 2) found administered growth factors (granulocyte-colony stimulating factor and granulocyte macrophage-colony stimulating factor) to affect neutrophil numbers only. The one study showed marked increases of neutrophil and platelet counts when granulocyte-colony stimulating factor was administered. Interleukin-3, administered alone or in combination with granulocyte macrophage stimulating factor had even less effect on myelopoiesis than the growth factors administered alone. Similarly (Liu et al., Cellular interactions in hemopoiesis, Blood Cells 1987; 13: 101-110 and Ettinghausen et al., Hematologic effects if immunotherapy with lymphokine-activated killer cells and recombinant interleukin-2 in cancer patients, Blood 1987; 69(6): 1654-1660), found that administering activated peripheral blood mononuclear cells and interleukin-2 to patients "emphasized" anemia and oesinophilia in patients receiving this therapy.

The present invention is also contemplated to include items of manufacture, which include separately packaged containers of one or more cytokine(s) and ionophore(s) as more fully described above. The container contents may be used to culture, and thereby activate, blood cells for use in the present therapeutic protocol. Instructions, such as on a label, may be present in the item of manufacture. A medium suitable for culturing blood cells may further be included.

Example 2

Treatment of Platelet Deficiency

This example described the treatment of a 1 year five month old female patient with idiopathic thrombocytopenic purpura. The patient was diagnosed with the disease at about 9 months.

The patient was first treated with conventional therapy of corticosteroids and intravenous infusions of immunoglobulin. Although the patient responded to the conventional treatment, the patient became completely dependent on the corticosteroid therapy. The maintain sufficient platelet levels, the patient had to receive increasingly higher doses of corticosteroids.

Then, the patient was treated with an activated cell based therapy as described herein. The treatment was the same as described in Example 1 except that only 20 mls of blood was drawn from the patient each time, rather than 40-50 mls. The patient was treated once a week for 9 weeks. Ex vivo activated cells were administered on day 1, day 8, day 15, day 22, day 29, day 35, day 42, day 49 and day 56. At the same time that immunotherapy with activated cells was initiated, corticosteroids and any other aspect of conventional therapy were completely withdrawn. The patient's platelet levels gradually improved during the treatment with activated cells as shown in FIG. 2. The patient had a lung infection at day 49 that correlated with a significant decrease in platelet number. After the patient recovered from the infection, the patient's platelet numbers went back to normal levels.

Example 3

Treatment of Thrombocytopenia

I. Patients

Adult patients with advanced-stage blood and metastatic solid cancer were enrolled in the present study (Table 2). Prior to the initiation of the study, patients were required to receive intensive chemotherapy in a combination with or without radiotherapy and experience severe myelosuppression defined as an absolute neutrophil count of $\leq 500$/mL, a hemoglobin concentration of $\leq 6.50$ gm/dL, and a platelet count of $\leq 20,000$/mL. Patients for the study were required to receive a combined therapy with G-CSF, erythropoietin and interleukin-11 for minimal period of at least 2 weeks. Also, selected patients were required to never recover from severe thrombocytopenia defined as a platelet count of $\leq 20,000$/mL. Patients were required to be dependent on prophylactic platelet transfusion, and patients with solid cancer were required to have bone metastases with severe pain requiring radiation therapy for pain relief.

TABLE 2

Characteristics of Patients

| | |
|---|---|
| Number of Patients | 12 |
| Age | |
| Median (range) | 55 (20-74) |
| Sex | |
| Male | 6 |
| Female | 6 |
| ECOG Score | 1 (0-2) |
| Diagnosis | |
| Non-small cell lung cancer | 4 |
| Non-Hodgkin's lymphoma | 3 |
| Colon Cancer | 3 |
| Acute Lymphocytic Leukemia | 2 |
| Prior Treatment | |
| Lumbar spine or pelvic radiation | 5 |
| No. of chemotherapy regimens | |
| Median (range) | 3 (1-5) |
| Duration of chemotherapy (weeks) | 24 (2-52) |
| Neutropenia | 6 |

Patients also needed to meet the following criteria to be eligible for the study: An Eastern Cooperative Oncology Group (ECOG) performance status of $\leq 2$ and no clinically significant cardiac or metabolic disease. Adequate hepatic and renal function (total bilirubin level 52.0 mg/dL, blood urea nitrogen (BUN) 530 mg/dL, serum creatinine level 52.0 mg/dL); normal left ventricular ejection fraction ($\geq 50$% on radionuclide ejection fraction [RNEF]).

Patients who were anticipated to or were receiving treatment with corticosteroids or anticoagulant drugs were excluded. Patients were also ineligible if they received any cytokine or investigational agent within 4 weeks before study entry. All patients were required to give a written informed consent. The protocol was approved by the Institutional Review Board of the hospitals.

II. Purification of Peripheral Blood Mononuclear and Cell Culture

ABO-matched allogeneic leukocytes were obtained from a healthy donor by leukopheresis and separated into peripheral blood mononuclear cells (PBMCs) by Ficoll-Hypaque centrifugation. The PBMCs were then cultured in RPMI-1640 (Life Technologies, Gaithersburg, Md.) with 10% fetal calf serum (FCS) (Jiangbin Bio-Reagents, Hangzhou, China) under sterile conditions at $3 \times 10^6$/ml for 48 h in the presence of IL-2 at 500 IU/mL (Ruixing Biopharmaceutical Inc., Beijing, China), GM-CSF at 200 U/mL (NCPC, Shijiazhuang, China), and the calcium ionophore A23187 at 100 ng/mL (Sigma, St. Louis, Mo.). The concentrations of IL-2 and GM-CSF were predetermined to have maximal stimulating activity on monocytes and T-cells, and FCS was chosen to add to the cell culture because FCS is thought to be stronger than human serum in supporting cell growth and differentiation of human immune cells. FCS used in this study had not been heat inactivated. Adherent cells were scraped off the plastic and harvested together with the non-adherent cells. The cells were then washed three times with saline before infusion.

III. Study Design

In this open label, nonrandomized clinical study, 12 eligible patients were enrolled. Patients were infused with a daily dose of $5 \times 10^7$ activated immune cells on day 0, 1 and 2, followed by resting periods on days 3 to 7. Such a cycle of 3 day's treatment and 4 day's resting was repeated once a week for maximum of 4 weeks. If at any time the platelet count increased to greater than 40,000/mL during the therapy, the treatment was discontinued.

Platelet counts were monitored at least three times weekly on nonconsecutive days. Platelets were transfused for a platelet count of $\leq 20,000$/mL. This prophylactic platelet transfusion policy was followed by all of the investigators in this study. Platelet counts were repeated 3 days later if the most recent count was greater than 40,000/mL.

Concomitant use of growth factor was not permitted to minimize the possibility of confounding effect on platelet recovery. Promethazine Hydrochloride was routinely given to patients just before the cell infusion began to reduce the side effects.

IV. Cytokine Analysis

Two days after the initiation of the cell culture, non-adherent cells were collected and washed twice with saline. Adherent cells were also washed gently twice with saline in the culture flask. The washed non-adherent cells were placed back into the same flask and fresh culture medium without cytokine and calcium ionophore was added to continue the culture for another three days. The supernatants were harvested and pooled for cytokine analysis using Luminex® xMAP® System (Luminex, Austin, Tex.).

V. Results

A. Cell Yield

During the 2 days of culture, some cells survived and expanded upon the stimulation with GM-CSF, IL-2, and calcium ionophore, meanwhile, unresponsive cells died. The differences in cell numbers before and after the cell culture were small.

B. Platelet Recovery

Figure 3:
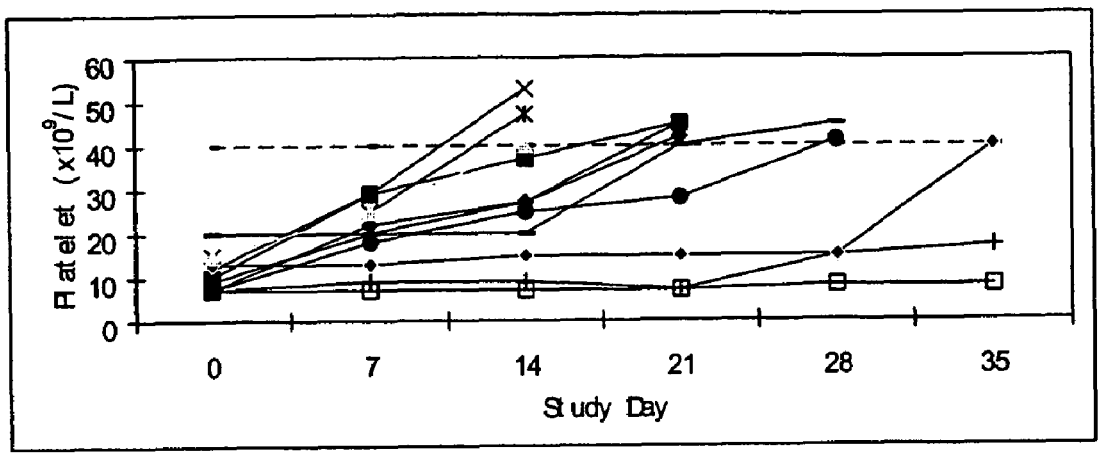
FIG. 3 is a plot of platelet counts after therapy with ex vivo activated immune cells for patients suffering from thrombocytopenia.

Ten patients with severe and prolonged thrombocytopenia responded to the therapy with their platelet counts increasing to the level of $\geq 40,000$/mL (FIG. 3). The other two patients did not respond. Referring to FIG. 3, which shows platelet counts after therapy with ex vivo activated immune cells (administered for consecutive three days starting on day 0, with treatment cycle repeated once a week for a maximum period of 4 weeks), each line shows the kinetics of platelet count of a patient. The dashed line indicates a platelet count of 40×10⁹ cells/mL. Of the ten patients who had platelet improvement, two received three treatments, three received six treatments, three received nine treatments and the other two received twelve treatments; Two out of twelve patients did not reach the end point of the therapy after twelve treatments.

C. Leukocyte Recovery

Figure 4:
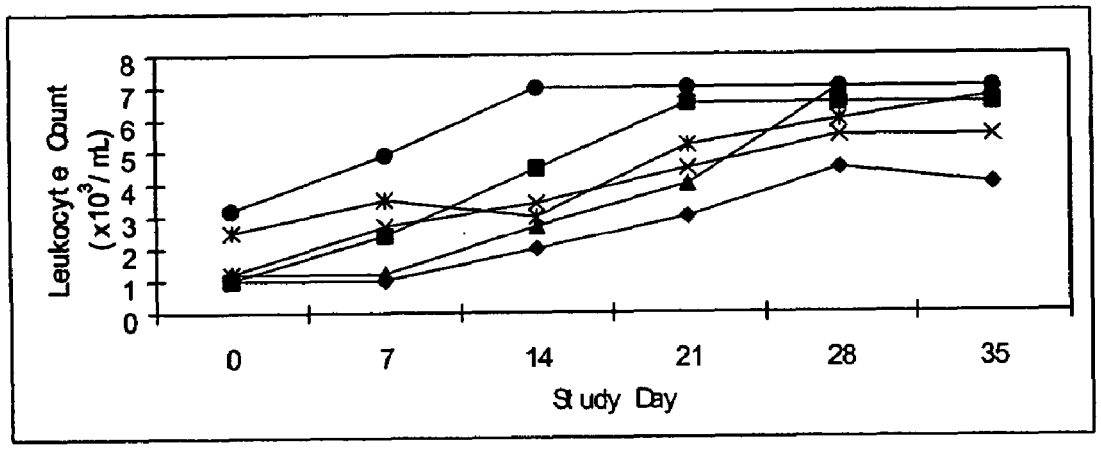
FIG. 4 is a plot of leukocyte counts after therapy with ex vivo activated immune cells for patients suffering from thrombocytopenia.

Six patients had lower leukocyte counts as well. Despite intensive treatment with G-CSF, their leukocyte counts remained lower than normal. As a result of the therapy with activated immune cells, all six patients' leukocyte counts improved and recovered to normal levels (FIG. 4). Referring to FIG. 4, which shows leukocyte counts after therapy with ex vivo activated immune cells (administered for consecutive three days starting on day 0, with treatment cycle repeated once a week for a maximum period of 4 weeks), it was found that the leukocyte recovery happened at an earlier time than that of platelets, typically in the range of one to a few weeks earlier for severe myelosuppressed patients. Two patients whose platelets did not improve as described above showed improved leukocyte counts. It was found in general that it takes more treatments and a longer time for platelet count to recover than that of leukocyte.

D. Cytokine Production

A group of cytokines were selected to determine whether these therapeutic cells produced multiple cytokines. As shown in Table 3, of 19 cytokines detected, 7 (IL-1b, IL-2, IL-6, IL-8, G-CSF, GM-CSF, MIP-1b) were at very high levels and 9 (IL-4, IL-5, IL-10, IL-13, IL-17, IL-18, IFN-gamma, and MCP-1) at modest levels, while the other 3 (IL-7, IL-12 and Eotaxin) at very low levels of secretion.

TABLE 3

| Cytokine | Concentration (pg/mL) | |
|---|---|---|
| | Medium Control | Supernatant |
| IL-1b | 0 | 2777.14 |
| IL-2 | 0 | 24342.96 |
| IL-4 | 0 | 164.87 |
| IL-5 | 0.14 | 141.51 |
| IL-6 | 0 | 334881 |
| IL-7 | 0 | 2.47 |
| IL-8 | 0 | too high |
| IL-10 | 3.54 | 415.2 |
| IL-12(p40) | 0 | 5.7 |
| IL-13 | 0.13 | 1167.55 |
| IL-17 | 0 | 50.74 |
| IL-18 | 0 | 8.97 |
| IFN-gamma | 0 | 634.69 |
| TNF-a | 0 | 461.04 |
| G-CSF | 0 | 178906 |
| GM-CSF | 19.7 | 198833.5 |
| MCP-1 | 0 | 215.54 |
| MIP-1b | 0 | 3202.82 |
| Eotaxin | 0 | 7.75 |

E. Clinical Tolerance

Therapy with ex vivo activated immune cells was well tolerated by all patients. No skin reactions, fluid retention, thromboembolic events, or organ toxicity were seen. The most common side effects were chills and fevers between 37 and 39° C., headache, nausea, vomiting and loss of appetite. These side effects were most often infusion-related and temporary, with most resolving within 24 h after cell infusion. Patients developing these symptoms were treated with conventional therapies accordingly. Promethazine hydrochloride was often given to minimize the side effects. No patients dropped out of the study because of the side effects.

F. Discussion

In this study, therapy with ex vivo activated blood cells, specifically immune cells, significantly enhanced the recovery of chemotherapy and radiotherapy-induced thrombocytopenia. As a result, patients with metastases to bone marrow had enough platelets to receive much needed radiotherapy for pain relief. Clinical development of many thrombopoietic cytokines has been limited because of their modest activity, or significant toxicity or neutralizing antibodies. Interleukin-11 is the only thrombopoietic cytokine approved by the U.S. Food and Drug Administration to date. Patients were carefully selected in this study to meet the criteria that patients had received but failed to respond to IL-11.

It was found that the ex vivo immunotherapy was effective not only for severe thrombocytopenia but also for neutropenia. Six patients with low leukocyte counts responded well to the therapy despite that G-CSF therapy had failed to enhance their leukocyte counts to normal levels. This result is in agreement with what has been seen in animal experiment (Huaiyu Chen, Lubo Wu, Jiayu Chen, Xiaohui Wang, Jing Li, Bo Xie, and Demao Yang. Ex Vivo Activated Immune Cells Promote Survival and Stimulate Multilineage Hematopoietic Recovery in Myelosuppressed Mice. Submitted.). The ability of the therapy to stimulate multilineages of blood production brings significant benefits to patients with severe and chronic myelosuppression.

G-CSF has been demonstrated to be highly effective for treatment of mild to modest neutropenia, however, it is less effective for severe and chronic blood deficiency. The recovery of severely damaged bone marrow may require multiple growth factors (perhaps partially unknown), working in concert. Without being bound to a particular theory of operation, it is possible that some presently unknown key factors are responsible, at least in part for the effectiveness of the present therapy. Ex vivo-activated immune cells used in present study secreted multiple cytokines and growth factors (Table 3). Some of the secreted cytokines such as GM-CSF, G-CSF, IL-1(Hestdal K, Jacobsen S E, Ruscetti F W, Dubois C M, Longo D L, Chizzonite R, Oppenheim J J, Keller J R. In vivo effect of interleukin-1 alpha on hematopoiesis: role of colony-stimulating factor receptor modulation. Blood. 15;80(10):2486-94, 1992.), IL-6(Rodriguez Mdel C, Bernad A, Aracil M. Interleukin-6 deficiency affects bone marrow stromal precursors, resulting in defective hematopoietic support. Blood. 1;103(9):3349-54. 2004.) and IL-8 (Fibbe W E, Pruijt J F, Velders G A, Opdenakker G, van Kooyk Y, Figdor C G, Willemze R. Biology of IL-8-induced stem cell mobilization. Ann N Y Acad Sci. 30;872:71-82, 1999) have been shown to be hematopoietic. It is also possible that the infused cells travel to the bone marrow, liver, and spleen to deliver growth factors to hematopoietic stem cells and to other precursor cells at close range. Moreover, they may also be able to remain in close proximity to the marrow for periods sufficient to affect microenvironment improvement. Another factor that might be responsible for the effectiveness of the present therapy is that cell contact between immune cells and hematopoietic cells may be essential for hematopoietic cell growth and differentiation. Previous experience in treating benzene-induced aplastic anemia with growth factors is that they motivate existing committed progenitor cell pool better and more rapidly than the present method, however they lack sustained effects on hematopoiesis in bone marrow. This Example describes a particular therapy is more advantageously effective for chronic diseases and suitable for a longer period of use (Jiayu Chen; Weiwei Liu; Xiaohuai Wang; Huaiyu Chen; Jinming Wu; Yi Yang; Lubo Wu;

Demao Yang. Ex Vivo Immunotherapy for Patients with Benzene-Induced Aplastic Anemia. Journal of Hematotherapy & Stem Cell Research. 12: 505-514, 2003).

The use of GM-CSF, IL-2, and calcium ionophore in culturing PBMCs may have completed cell activation and differentiation. Calcium ionophore is a strong and nonspecific cell-stimulating agent; its use is thought to enhance the effects of GM-CSF and IL-2. GM-CSF, IL-2, IL-12 and calcium ionophore together have been shown to induce monocytes into cells that resemble the phenotype of dendritic cells (Bedrosian I, J G Roros, S Xu, HQ Nguyen, F Engels, M B Faries, G K Koski, P A Cohen and B J Czerniecki. Granulocyte-macrophage colony-stimulating factor, interleukin-2, and interleukin-12 synergize with calcium iono-phore to enhance dendritic cell function. J Immunother 23:311-320, 2000). However, most protocols of making mature and potent dendritic cells have an optimal culture time of 6-8 days. The therapy uses cells from 2-day culture, presumably at the peak of cell activation of cytokine production; additionally, this therapy is more practical and easier to handle. The ability of the present therapy to stimulate multiple lineages of blood cells, in particular platelets, offers some advantages over currently available therapeutic methods, in particular, growth factors.

Example 4

Treatment of Myelosuppression

I. Induction of Myelosuppression

Ten-week-old female BALB/c mice (Animal Center of Sun Ye Xian University, Guangzhou, China) were divided into groups at ten mice per group. Myelosuppression was induced by i.p. injection of carboplantin at 1.5 mg/mouse immediately followed by a single dose of total body irradiation at 300 cGy. The amount of carboplantin and irradiation used to induce myelosuppression was predetermined by testing various dose combinations in mice to have death rates between 80% and 100%.

II. Cells and Cell Culture

Human leukocytes were obtained by leukopheresis of healthy human donors and separated into peripheral blood mononuclear cells (PBMCs) by Ficoll-Hypaque centrifugation. The PBMCs were then cultured in RPMI-1640 (Life Technologies, Gaithersburg, Md.) with 10% fetal calf serum (FCS) (Jiangbin Bio-Reagents, Hangzhou, China) under sterile conditions at $3 \times 10^6$/ml for 48 h in the presence of IL-2 at 500 IU/ml (Ruixing Biopharmaceutical Inc., Beijing, China), GM-CSF at 200 U/ml (NCPC, Shijiazhuang, China), and the calcium ionophore A23187 at 100 ng/ml (Sigma, St. Louis, Mo.). FCS was chosen to add to the cell culture because FCS is thought to be stronger than human serum in supporting cell growth and differentiation of human immune cells. The FCS used in this study had not been heat inactivated because it may contain multiple growth factors beneficial to the activation of the cultured cells. Adherent cells were scraped off the plastic and harvested together with the non-adherent cells. The cells were then washed three times with saline before injected to mice.

Separation of non-adherent from adherent cells was carried out by the ability of adherent cells to adhere to the plastic. PBMCs were incubated in the absence of growth factors and calcium ionophore for 3 hours, and non-adherent cells were removed gently from the culture flask. The adherent and non-adherent cells were then cultured separately for 2 days in the presence of GM-CSF plus calcium ionophore and IL-2 plus calcium ionophore respectively.

Spleens from normal BALB/c mice were homogenized and red blood cells were lysed with distilled water. The remaining cells were cultured with mouse GM-CSF at 1 ng/ml, IL-2 at 2 ng/ml (both from eBioscience, San Diego, Calif.) and calcium ionophore A23187 for two days.

III. Study Groups and Treatments

Myelosuppressed mice were treated with ex vivo activated syngeneic mouse spleen cells and human PBMCs respectively before and after chemotherapy and irradiation respectively. For therapy after induction of myelosuppression, mice were injected intravenously four times on day 0, 2, 4 and 6.3 doses of cells at $1 \times 10^5$, $1 \times 10^6$ and $1 \times 10^7$ cells per mouse were tested. A single injection of $2 \times 10^7$ cells 3 hours after the induction of myelosuppression was also tested.

For prophylaxic therapy, a single injection of $2 \times 10^7$ activated cells per mouse was performed 24 hours before the induction of myelossupression.

IV. Cytokine Analysis

Two days after the initiation of the cell culture, non-adherent cells were collected and washed twice with saline while adherent cells were also washed gently twice with saline in the culture flask. The washed non-adherent cells were placed back into the same flask and fresh culture medium without cytokine and calcium ionophore was added to continue the culture for another three days. The supernatants were harvested and pooled for cytokine analysis using Luminex® xMAP® System (Luminex, Austin, Tex.).

V. Peripheral Blood Analysis

To determine recovery post-chemotherapy and irradiation, peripheral blood was collected from the tail vein of mice at day 8, 15 and 22. Full blood count was performed on a Thechnicon H-1E (Technicon Instruments Corp, Tarrytown, N.Y.) calibrated for mouse blood.

VI. Stem Cell Mobilization by Activated Human Blood Cells

Table 4 indicates that there was a certain level of stem cell mobilization by this cell therapy. Xenogeneic human cells cultured with IL-2, GM-CSF and calcium ionophore were given to normal BALB/c female mice, 1×107 per mouse, once a day for consecutive 3 days. Two days after the last injection, peripheral blood was taken by a Retro-orbital puncture. Red blood cells were quickly lysed with water and the 10×PBS was added to rebalance the salt concentration to normal levels. The remaining cells were incubated with anti-mouse CD34 PE (BD Biosciences Pharmingen, San Diego) monoclonal antibodies on ice for 20 minutes. The cells were washed 3 times with PBS after incubation and then analyzed on a FACSCALIBUR (Becton Dickinson [BD]; San Jose, Calif.). Samples were drawn into the flow cytometer using forward side scatter and side scatter, as gating parameters, along with debris subtraction techniques to determine the characteristics of the cells. A total of 30,000 events were counted to identify the mononuclear cell fraction. Analysis was done using CELLQUEST software (BD). Cells from untreated normal mice as controls. As shown in Table 4, the population in CD34 expressing cells was increase from 0.34% (Standard Error) in normal mice to 1.63% in mice treated with activated cells, indicating ex vivo activated xenogeneic human immune cells' ability to stimulate and mobilize stem cells from bone marrow into peripheral blood circulation.

TABLE 4

Cell therapy increases stem cell numbers of peripheral blood.

|  | Normal Mice | Treated Mice on Day 5 |
|---|---|---|
| % CD4 Positive Cells | 0.35 ± 0.22 | 1.55 ± 0.45 |

Figure 7:
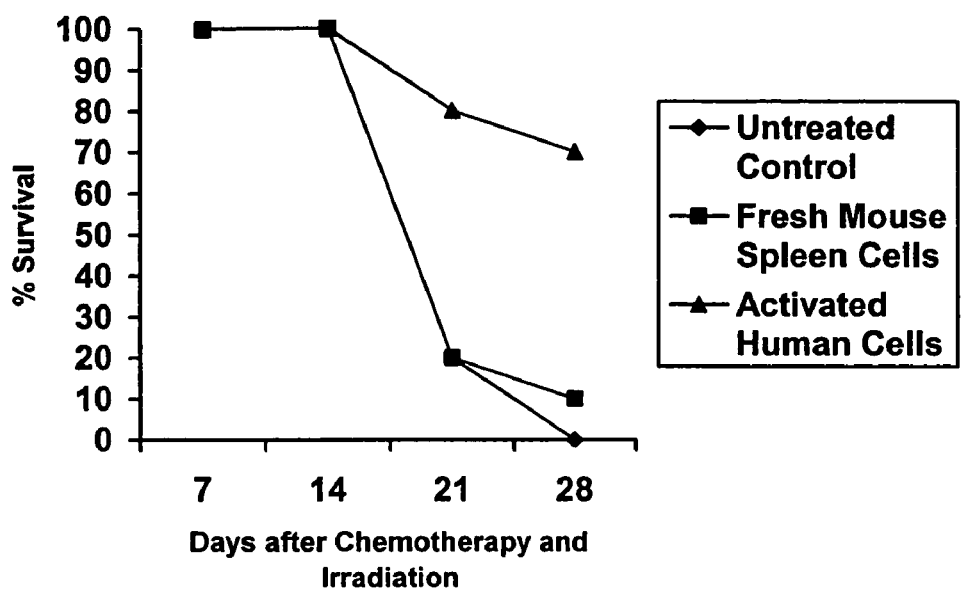
FIG. 7 is a plot of the results of using an alternative cell culturing condition showing survival in response to ex vivo activated syngeneic and xenogeneic immune cells administered after the induction of myelosuppression.

VII. Rescue of Myelosuppressed Mice Using ex vivo Blood Cells Cultured in the Absence of Ionophores GM-CSF and anti-human CD3 antibodies were used to in culture and activate PBMCs that were successfully used to rescue myelosuppressed mice, as shown in FIG. 7. The cells were collected and cultured as described herein, except they were cultured with GM-CSF and mouse anti-human CD3 monoclonal antibodies at 1 µg/ml for two days. The induction of myelosuppression was as previously described herein. Mice were injected intravenously three times immediately, two 48 hours and 96 hours after the induction of chemotherapy and irradiation at dose of $1\times10^6$ cells per mouse. As shown in FIG. 7, this culture process was effective in activating blood cells to treat myelosuppression. Further, xenogeneic human cells were successfully used in the mouse.

A variety of culture conditions with various combinations of cytokines and cell activating agents have similar effects on hematopoiesis. The combination of IL-2, GM-CSF and calcium ionophore used to activate mixed populations of peripheral blood mononuclear cells has been effective, but other cultures conditions with different cell activating agents are also effective. Thus, the culture conditions for practicing the embodiments set forth herein are not limited to use of one or a combination of ionophore, GM-CSF and IL-2.

VIII. Results

A. Short and Long-Term Survival

Figure 5:
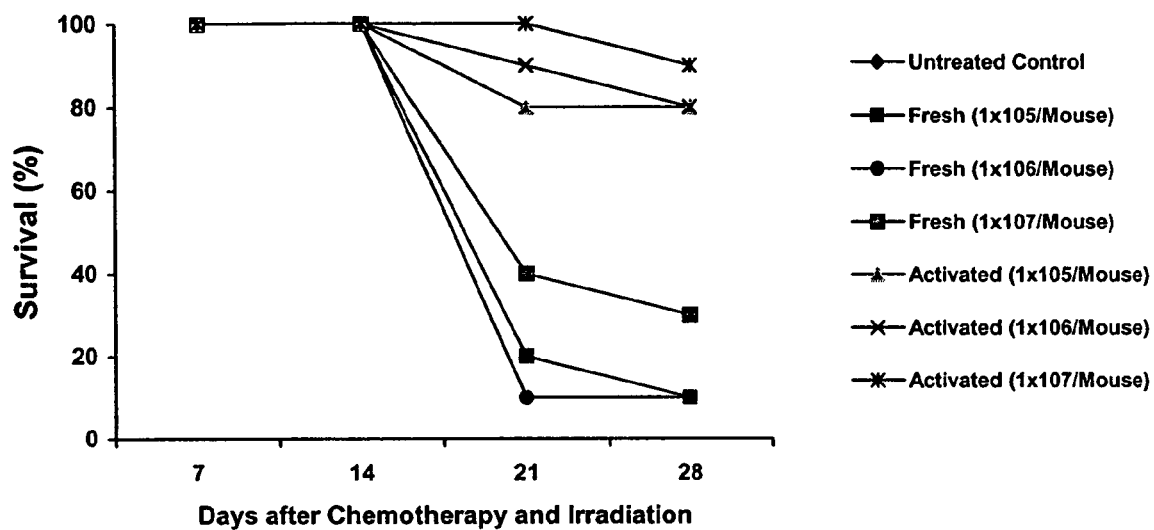
FIG. 5 is a plot of survival in response to ex vivo activated immune cells administered after the induction of myelosuppression.

Referring to FIG. 5, which shows that ex vivo activated syngeneic mouse spleen cells promote survival, myelosuppressed mice received 4 treatments with ex vivo activated mouse spleen cells immediately, 2, 4 and 6 days after the induction of myelosuppression. Myelosuppressed mice received four intravenous injections of activated mouse spleen cells and human PBMCs at 3 doses on day 0, 2, 4 and 6 after chemotherapy and irradiation. Control mice received fresh mouse spleen cells without ex vivo activation. As FIG. 5 shows, untreated control mice and mice receiving fresh mouse spleen cells had low survival rates between 0 and 30%. In contrast, activated mouse spleen cells significantly increased the survival rate of myelosuppressed mice to 80-100%. There was no significant difference in survival rates among the treatment groups. It was noted that mice receiving four injections of fresh mouse spleen cells at $1\times10^7$ per mouse had slightly higher survival rate than other control groups. Four treatments with xenogeneic human cells had similar effects on survival in myelosuppressed mice (data not shown).

Figure 6:
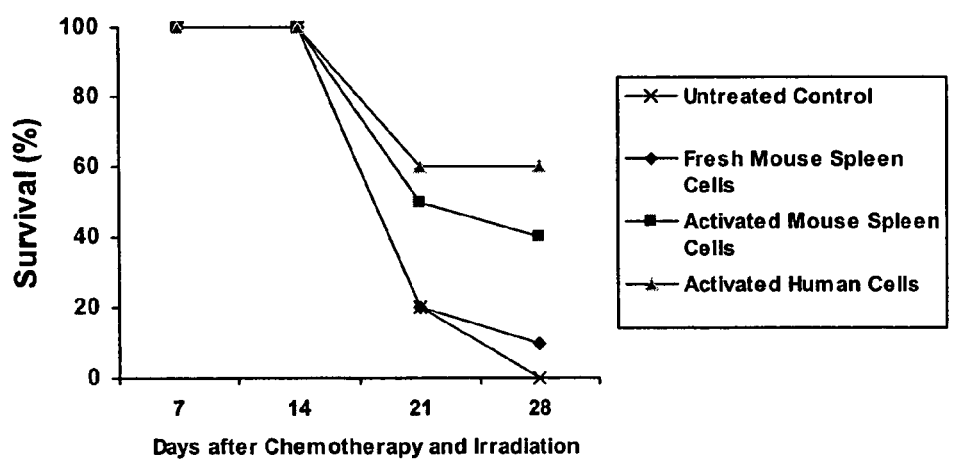
FIG. 6 is a plot of survival in response to ex vivo activated syngeneic and xenogeneic immune cells administered after the induction of myelosuppression.

Referring to FIG. 6, which shows that single injection of ex vivo activated syngeneic spleen cells and xenogeneic human immune cells enhanced survival, myelosuppressed mice received single injection of $2\times10^7$ ex vivo activated cells immediately after the induction of myelosuppression. Four treatments with ex vivo activated cells rescued significant portion of myelosuppressed mice, experiments were performed to see whether a single treatment would be able to improve the survival rate. The result showed that a single injection of activated cells at $2\times10^7$ per mouse immediately after chemotherapy and irradiation also enhanced survival in myelosuppressed mice and hematological recovery (FIG. 6), although the increase in survival rate was not as high as that with four treatments.

The myelosuppressed mice which were rescued by activated immune cells were followed up to 6 months for long-term survival. It was found that all rescued mice survived well 6 month after the therapy. Despite the strong effects of the therapy administrated after the induction of myelosuppression on survival, prophylactic treatment of mice before chemotherapy and irradiation failed to rescue mice (data not shown).

Figure 8:
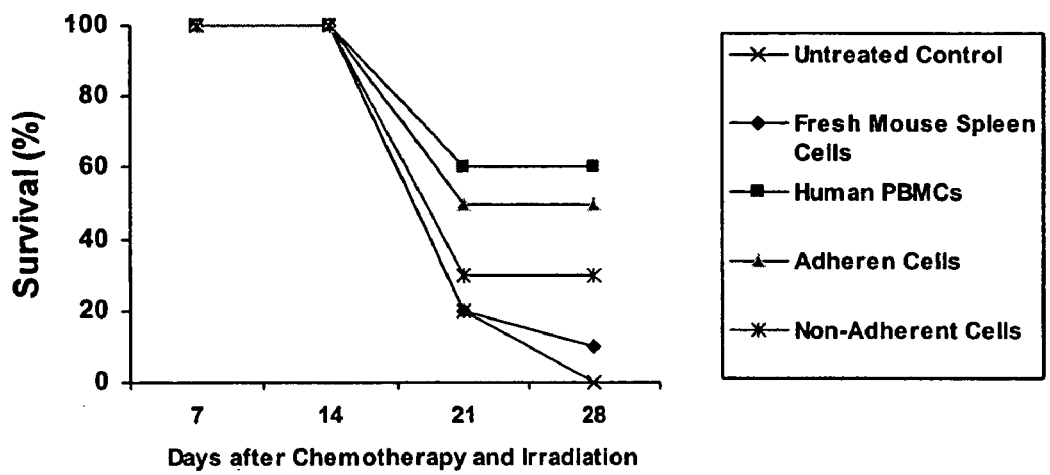
FIG. 8 is a plot of survival in response to ex vivo activated immune cells administered after the induction of myelosuppression showing the role of adherent and nonadherent cells.

Referring to FIG. 6, myelosuppressed mice received single injection of $2\times10^7$ ex vivo activated cells immediately after the induction of myelosuppression. To further investigate the roles played by different subpopulations of activated immune cells in rescuing myelosuppressed mice, human adherent and non-adherent immune cells were separately cultured and injected into myelosuppressed mice. As shown in FIG. 8, both populations were able to enhance survival of the myelosuppressed mice, however, adherent cells were more potent than non-adherent cells.

B. Recovery of Blood Count

Figure 9:
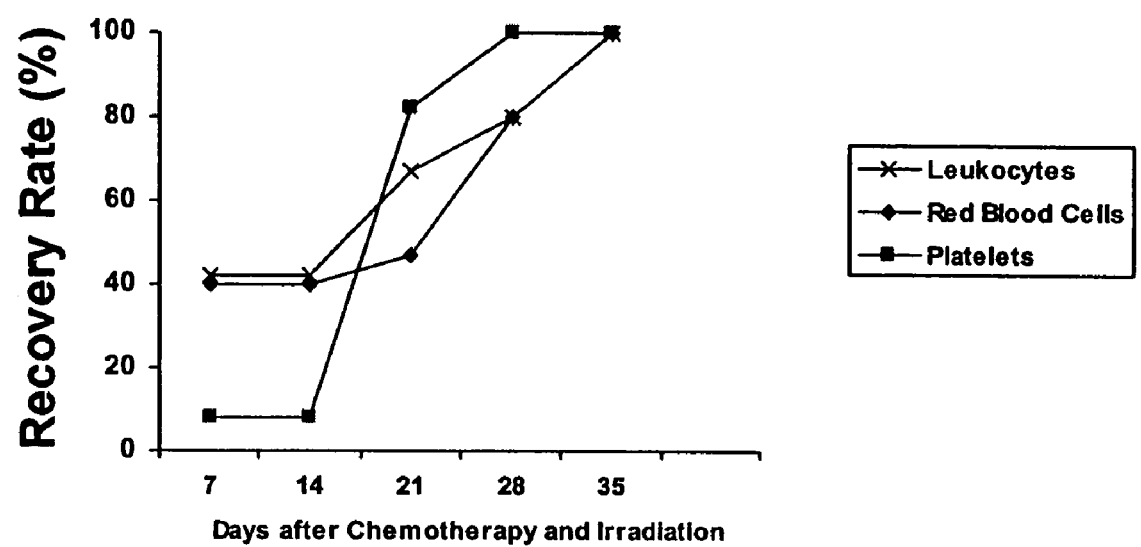
FIG. 9 is a plot showing recovery rates in response to ex vivo activated xenogeneic immune cells.

Total blood count was performed before and after the therapy. Referring to FIG. 9, myelosuppressed mice received injection of $1\times10^7$ ex vivo activated human cells immediately, 2, 4 and 6 days after the induction of myelosuppression. The blood counts before chemotherapy and irradiation were designated as 100%. FIG. 9 shows the recovery curves of the mice receiving $1\times10^7$ cells for 4 times. Blood counts of the treated mice started to improve at week 3 and fully recovered at week 5. It was noted that platelet counts improved more significantly one week before those of leukocyte and erythrocyte. In general, it was found that the speed of recovery of blood counts resulting from the therapy was correlated well with the dosage and number of treatments (data not shown) and that once the blood counts began to improve, full recovery happened within 2 to 3 weeks.

C. Discussion

The results of this Example indicate that cell therapy with ex vivo activated immune cells is effective in treating chemotherapy and irradiation-induced myelosuppression. Although currently available drugs of G-CSF, GM-CSF, erythropoietin and IL-11 are effective for mild to modest myelosuppression, they are often ineffective for severe and chronic myelosuppression and, in particular, thrombocytopenia as a result of high-dose chemotherapy in cancer patients. Cell therapy using activated immune cells has certain advantages over growth factors in treatment of myelosuppression. First, activated cells apparently produce multiple growth factors for hematopoiesis, and these growth factors, working in concert, may have a synergistic combined effect. It is also possible that some presently unknown key factors are responsible, at least in part for the effectiveness of this therapy. Without being bound to a particular theory, ex vivo-activated immune cells and subsequent in vivo immune responses resulting from the cell infusion may contribute to the production of the growth factors. Second, the infused cells may travel to bone marrow, liver, and spleen to deliver growth factors to hematopoietic stem cells and other precursor cells at close range. Moreover, they may also be able to remain in close proximity to the marrow for periods sufficient to effect microenvironment improvement. Third, cell contact between infused cells and hematopoietic cells may be essential for hematopoietic cell growth and differentiation.

The cytokines and chemokines produced by ex vivo activated immune cells show some interesting characteristics, in which IFN-gamma, IL-12, IL-4 and IL-10, the four major cytokines representing Th1 and Th2 subsets of T helper cells respectively, were at relatively low levels in comparison with IL-1β, IL-6, IL-8, G-CSF and GM-CSF, Because numerous modifications of this invention may be made without departing from the spirit thereof, the scope of the invention is not to be limited to the embodiments illustrated and described. Rather, the scope of the invention is to be determined by the appended claims and their equivalents.

TABLE 1

Hematological Profiles of Patients Before and After Cell-Based Immune Therapy.

| Patients | Age/Sex | No. of Treatment | Disease Type | WBC ($\times 10^3$/mL) | RBC ($\times 10^6$/mL) | HGB (g/dl) | PLT ($\times 10^3$/mm$^3$) | WBC ($\times 10^3$/mL) | RBC ($\times 10^6$/mL) | HGB (g/dl) | PLT ($\times 10^3$/mm$^3$) |
|---|---|---|---|---|---|---|---|---|---|---|---|
| HC | 32/F | 6 | Acute   | 2.7 +/− 0.2 | 1.2 +/− 0.1 | 4.0 +/− 0.3  | 28 +/− 3    | 3.8 +/− 0.25 | 2.0 +/− 0.2  | 7.0 +/− 0.3  | 43 +/− 3    |
| YM | 29/F | 4 | Chronic | 3.6 +/− 0.3 | 3.8 +/− 0.5 | 11.1 +/− 0.4 | 99 +/− 11   | 6.7 +/− 0.3  | 3.9 +/− 0.4  | 12.7 +/− 0.5 | 182 +/− 17  |
| TB | 33/F | 4 | Acute   | 3.2 +/− 0.2 | 2.3 +/− 0.3 | 8.4 +/− 0.4  | 47 +/− 5    | 4.7 +/− 0.3  | 3.2 +/− 0.3  | 11.5 +/− 0.7 | 107 +/− 11  |
| LC | 25/M | 4 | Acute   | 1.4 +/− 0.2 | 1.6 +/− 0.3 | 5.7 +/− 0.3  | 16 +/− 7    | 5.7 +/− 0.2  | 4.8 +/− 0.3  | 13.5 +/− 0.7 | 135 +/− 14  |
| YX | 25/F | 4 | Chronic | 2.5 +/− 0.3 | 2.7 +/− 0.2 | 8.2 +/+ 0.4  | 22 +/− 3    | 3.5 +/− 0.3  | 2.8 +/− 0.2  | 9.8 +/− 0.5  | 100 +/− 10  |
| JX | 29/F | 5 | Acute   | 2.7 +/− 0.7 | 3.0 +/− 0.2 | 8.1 +/− 3.4  | 44 +/− 18   | 4.5 +/− 0.7  | 3.6 +/− 0.1  | 12.0 +/− 0.4 | 126 +/− 8   |
| ZL | 41/F | 4 | Chronic | 3.1 +/− 0.6 | 4.0 +/− 0.6 | 12.6 +/− 1.9 | 154 +/− 35  | 3.7 +/− 0.1  | 4.3 +/− 0.02 | 13.2 +/− 1.3 | 187 +/− 21  |
| SC | 29/F | 4 | Chronic | 2.4 +/− 0.3 | 2.6 +/− 0.1 | 10.0 +/− 3.5 | 54 +/− 4    | 2.8 +/− 0.2  | 2.9 +/− 0.2  | 11.0 +/− 0.3 | 71 +/− 8    |

The hematological parameters were measured and analyzed for five consecutive days before and after the therapy. Data are expressed as means +/− standard deviation. WBC indicates white blood cells; RBC indicates red blood cells; HGB indicates hemoglobin; PLT indicates platelets.

which are known to have potent hematopoietic activities. The finding that xenogeneic human cells were as effective as syngeneic mouse cells suggested the mechanism of the therapy is not MHC-dependent or mediated.

The use of IL-2 in cell culture may have helped T-Cells survive and become stimulated. Without being bound to a particular theory of operation, IL-2 activated T cells should have longer viability and cytokine production in vivo than T cells activated by other agents like anti-CD3 monoclonal antibodies or PHA or ConA. GM-CSF is used to stimulate myeloid cells for the same reason. To ensure full activation of T and myeloid cells, calcium ionophore may be used to co-stimulate with IL-2 and GM-CSF.

GM-CSF and calcium ionophore together have been shown to induce monocytes into cells that resemble the phenotype of dendritic cells. However, most protocols of making mature and potent dendritic cells have an optimal culture time of 6-8 days. Therapies are described herein that use cells from 2-day culture, presumably at the peak of cell activation of cytokine production; additionally, these therapies are more practical and easier to implement. Further, there is no need to undertake special steps to prepare purified preparations of stem cells or highly enriched monocytes preparations. Moreover, such protocols have been directed to exposing cells to culture factors at certain concentrations and durations for stimulating cells to achieve a phenotype for immunological purpose, for example to express a certain cell surface antigen. Such processes do not enable the present therapies, which are not directed to achieving such phenotypes or to measuring or achieving the expression of such markers. Further, the differences in the types of cells cultured and duration of culturing will not necessarily achieve the state of activation that is brought about by the blood cell activation processes described herein. Moreover, the present therapies include treatments for myelosuppression and/or hematopoiesis, which are treatments that have not been indicated by these other protocols.

All publications, patents, patent applications, and other documents cited herein are hereby incorporated by reference in their entirety. In the case of conflict, the present specification shall prevail.

The invention claimed is:

1. A process of treating a myelosuppressed patient having blood deficiencies associated with the myelosuppression, comprising culturing blood cells ex vivo in the presence of (a) a cytokine and a calcium ionophore or (b) granulocyte macrophage colony stimulating factor and anti-CD3 antibody to thereby activate the blood cells, and administering the ex vivo cultured activated blood cells to the patient to increase concentrations of blood components thereby treating the myelosuppression, wherein the blood cells are from a spleen or are peripheral blood mononuclear cells.

2. The process of claim 1 wherein the patient is a human.

3. The process of claim 1 wherein the myelosuppression is severe.

4. The process of claim 1 wherein the blood deficiencies comprise neutropenia, leucopenia, thrombocytopenia, or a combination thereof.

5. The process of claim 1 wherein the blood deficiencies comprise severe or chronic thrombocytopenia.

6. The process of clam 1 wherein the myelosuppression is at least partially caused by a cancer treatment.

7. The process of claim 6 wherein the cancer treatment comprises radiation or chemotherapy.

8. The process of claim 1 wherein the calcium ionophore comprises A23187.

9. The process of claim 1 wherein the cytokine comprises interleukin-2.

10. The process of claim 1 wherein the cytokine comprises macrophage-colony stimulating factor.

11. The process of claim 1 wherein the culturing is performed for less than about 2 days.

12. The process of claim 1 wherein the blood cells are autologous to the patient.

13. The process of claim 1 wherein the blood cells are allogeneic to the patient.

14. The process of claim 1 wherein the blood cells are separated from blood sera by centrifugation.

15. The process of claim 1 wherein the blood cells are cultured in the presence of a mammalian serum.

16. The process of claim 1 wherein the blood cells are cultured in the presence of fetal bovine serum.

17. The process of claim 1 wherein the blood cells are from an immunologically acceptable donor.

18. The process of claim 1 wherein the administering is performed by intravenous injection.

19. The process of claim 1 wherein the administering of the ex vivo activated blood cells comprises the administration of multiple doses.

20. The process of claim 19 wherein the multiple doses are administered over at least about 4 weeks.

21. The process of claim 1 wherein the cells are cultured in serum-less medium.

22. The process of claim 1 wherein purified peripheral blood mononuclear cells are activated to form the ex vivo cultured blood cells.

23. The process of claim 1 wherein the blood cells are cultured in the presence of a calcium interleukin, a cell stimulating factor and an ionophore.

24. The process of claim 1 wherein the blood cells comprise at least 3 types of cells.

25. A process of treating a human patient having blood deficiencies associated with a cancer treatment, comprising culturing blood cells in the presence of a cytokine and at least one of a calcium ionophore or an anti-CD3 antibody to thereby activate the blood cells, and administering a therapeutically effective amount of the ex vivo cultured activated blood cells to the patient to increase concentrations of blood components thereby treating blood deficiencies associated with a cancer treatment, wherein the blood cells are from a spleen or are peripheral blood mononuclear cells.

26. The process of claim 25 wherein the blood deficiencies comprise neutropenia, leucopenia, severe thrombocytopenia, chronic thrombocytopenia, or a combination thereof.

27. The process of claim 25 wherein the cancer treatment comprises radiation or chemotherapy.

28. The process of claim 25 wherein the culturing is performed for less than about 2 days.

29. The process of claim 25 wherein the blood cells are autologous or allogeneic.

30. The process of claim 25 wherein the blood cells are separated from blood sera by centrifugation.

31. The process of claim 25 wherein the blood cells are peripheral blood mononuclear cells.

32. The process of claim 25 wherein purified peripheral blood mononuclear cells are activated to form the ex vivo cultured blood cells.

33. The process of claim 25 wherein the blood cells are cultured in the presence of a calcium interleukin, a cell stimulating factor and an ionophore.

34. The process of claim 25 wherein the blood cells comprise at least 3 types of cells.

* * * * *